(12) United States Patent
Venkatasubramanian et al.

(10) Patent No.: US 12,336,429 B2
(45) Date of Patent: Jun. 17, 2025

(54) THERMOTACTILE STIMULATION PROSTHESIS

(71) Applicant: The Johns Hopkins University, Baltimore, MD (US)

(72) Inventors: Rama Venkatasubramanian, Cary, NC (US); Luke E. Osborn, Baltimore, MD (US); Robert S. Armiger, Catonsville, MD (US); Meiyong Himmtann, Sykesville, MD (US); Jonathan M. Pierce, North Eldersburg, MD (US)

(73) Assignee: The Johns Hopkins University, Baltimore, MD (US)

( * ) Notice: Subject to any disclaimer, the term of this patent is extended or adjusted under 35 U.S.C. 154(b) by 335 days.

(21) Appl. No.: 18/071,789

(22) Filed: Nov. 30, 2022

(65) Prior Publication Data

US 2023/0106799 A1      Apr. 6, 2023

Related U.S. Application Data

(60) Continuation-in-part of application No. 17/544,391, filed on Dec. 7, 2021, now Pat. No. 11,532,778, which is a division of application No. 17/038,614, filed on Sep. 30, 2020, now Pat. No. 11,227,988.

(51) Int. Cl.
| | |
|---|---|
| *H10N 10/13* | (2023.01) |
| *F25B 21/02* | (2006.01) |
| *H10N 10/852* | (2023.01) |
| *H10N 19/00* | (2023.01) |

(52) U.S. Cl.
CPC ............. *H10N 10/13* (2023.02); *F25B 21/02* (2013.01); *H10N 10/852* (2023.02); *H10N 19/00* (2023.02); *H10N 19/101* (2023.02)

(58) Field of Classification Search
CPC ...... H10N 10/13; H10N 10/852; H10N 19/00; H10N 19/101; A61F 2/54; A61F 2002/5063; A61F 2002/543
See application file for complete search history.

(56) References Cited

U.S. PATENT DOCUMENTS

| | | |
|---|---|---|
| 5,091,756 A | 2/1992 | Iga et al. |
| 6,603,184 B2 | 8/2003 | Lin et al. |
| 7,872,253 B2 | 1/2011 | Ohta et al. |
| 8,940,995 B2 | 1/2015 | Park et al. |
| 9,269,883 B2 | 2/2016 | Baniecki et al. |
| 10,378,099 B2 | 8/2019 | Sarakinos et al. |
| 2002/0027238 A1 | 3/2002 | Lin et al. |

(Continued)

OTHER PUBLICATIONS

Zhaocun Zhang et al., "Conduction block of mammalian myelinated nerve by local cooling to 15-30° C. after a brief heating," J Neurophysiol 115 (2016) pp. 1436-1445.

(Continued)

*Primary Examiner* — Golam Mowla
(74) *Attorney, Agent, or Firm* — Noah J. Hayward

(57) ABSTRACT

A thermotactile stimulation prosthesis includes a prosthesis extremity having a prosthesis interface configured for attachment to a human limb, and a thermoelectric actuator array coupled to the prosthesis interface and configured to establish a noninvasive thermoneural human-machine interface capable of providing sensations of temperature to the human limb.

16 Claims, 17 Drawing Sheets

(56) References Cited

U.S. PATENT DOCUMENTS

| | | | |
|---|---|---|---|
| 2005/0139250 A1* | 6/2005 | DeSteese | H10N 10/852 |
| | | | 136/212 |
| 2006/0086118 A1 | 4/2006 | Venkatasubramanian et al. | |
| 2009/0173932 A1 | 7/2009 | Ohta et al. | |
| 2009/0182392 A1* | 7/2009 | Woolaston | A61N 1/36038 |
| | | | 607/57 |
| 2011/0277803 A1* | 11/2011 | Grande | G01K 7/028 |
| | | | 136/200 |
| 2012/0312030 A1 | 12/2012 | Lu | |
| 2019/0099286 A1* | 4/2019 | Myers | A61F 2/7812 |
| 2019/0242636 A1 | 8/2019 | Tsuno | |

OTHER PUBLICATIONS

Maohui Luo et al., "High-density thermal sensitivity maps of the human body," Building and Environment 167 (2020) 106435, pp. 1-12.

Rama Venkatasubramanian et al. "Thin-film thermoelectric devices with high room-temperature figures of merit," Nature, vol. 413 (2001), pp. 597-602.

\* cited by examiner

THERMOTACTILE STIMULATION PROSTHESIS

CROSS-REFERENCE TO RELATED APPLICATIONS

This application is a continuation-part of prior-filed, co-pending application Ser. No. 17/544,391 filed on Dec. 7, 2021, which is a divisional of prior-filed U.S. application Ser. No. 17/038,614 filed on Sep. 30, 2020 and which issued as U.S. Pat. No. 11,227,988 on Jan. 18, 2022, the contents of each of which are herein incorporated by reference in their entireties.

STATEMENT OF GOVERNMENTAL INTEREST

This invention was made with Government support under contract number HU0001-15-2-0028 awarded by the Uniformed Services University of the Health Sciences (USU). The Government has certain rights in the invention.

BACKGROUND

This disclosure relates generally to thermotactile stimulation prostheses and, more particularly, to thermotactile stimulation prostheses including thermoelectric devices such as fast-rate thermotactile actuators.

Thermoelectric devices utilize a thermoelectric effect to directly convert an electric power input into a temperature differential to generate a heating effect or cooling effect. This thermoelectric effect, referred to as the "Peltier effect," is achieved by connecting together two different thermoelectric materials, one being a p-type material and the other being an n-type material, with a metal interconnect to form an electrical junction. Applying a voltage across the junction induces a current flow, thereby cooling at this junction (producing a cooling effect) while rejecting heat at the opposite end of the junction (producing a heating effect).

However, attempts to improve conventional thermoelectric devices for applications requiring reduced device packaging and enhanced figures of merit at practical temperatures, as well as high heating/cooling power density and speed, have been unsuccessful in the past. Thus, what is needed is an improved thermoelectric device having these, and other, improvements.

BRIEF DESCRIPTION

According to a non-limiting example embodiment, a thermotactile stimulation prosthesis includes a prosthesis extremity having a prosthesis interface configured for attachment to a human limb, and a thermoelectric actuator array coupled to the prosthesis interface and configured to establish a noninvasive thermoneural human-machine interface capable of providing sensations of temperature to the human limb.

According to another non-limiting example embodiment, an interactive reality device includes a hollow shell configured to fit with a human appendage. The hollow shell includes an outer shell surface and an inner shell surface, the inner shell surface opposing the outer shell surface, the outer and inner shell surfaces surrounding an inner void configured to receive the human appendage. The interactive reality device further includes a plurality of thin-film thermoelectric (TFTE) actuators disposed on the inner shell surface, with the plurality of TFTE actuators being configured to establish a noninvasive thermoneural human-machine interface capable of providing sensations of temperature to the human appendage.

Additional features and advantages are realized through the techniques of the present disclosure. Other embodiments and aspects of the disclosure are described in detail herein. For a better understanding of the disclosure with the advantages and the features, refer to the description and to the drawings.

BRIEF DESCRIPTION OF THE DRAWINGS

The subject matter is particularly pointed out and distinctly claimed in the claims at the conclusion of the specification. The forgoing and other features and advantages of the non-limiting example embodiments described herein are apparent from the following detailed description taken in conjunction with the accompanying drawings, in which:

DETAILED DESCRIPTION

Figure 1:
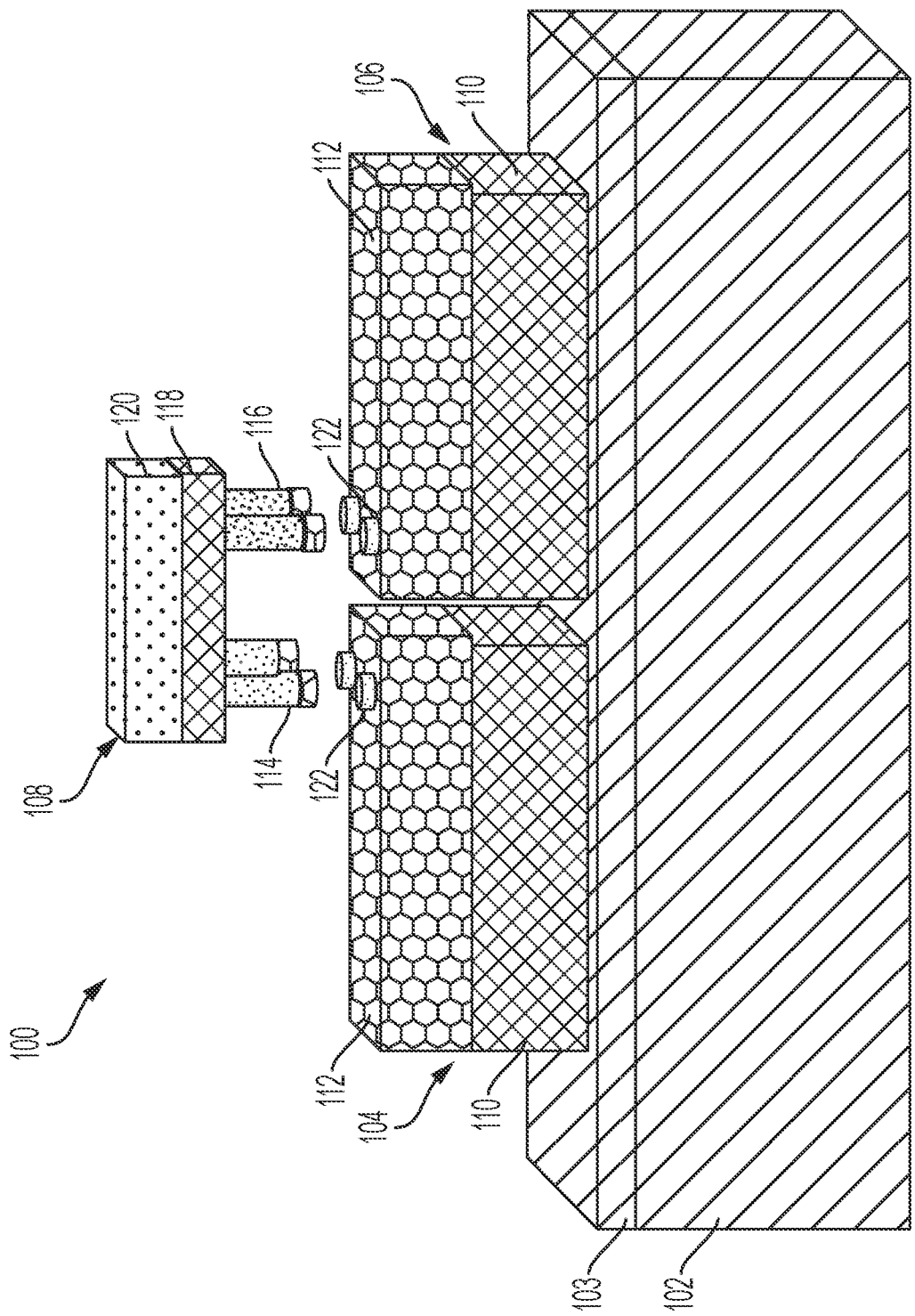
FIG. 1 is a block diagram illustrating a fast-rate thermoelectric actuator according to a non-limiting embodiment.

The performance of a thermoelectric device is typically based on the energy conversion efficiency (for both heating and cooling) of the device's thermoelectric material. This efficiency is determined by the material's "figure of merit" (ZT), which is defined by the following equation:

$$ZT = \frac{\alpha^2 T}{\rho K_t},$$

where $\alpha$, T, $\rho$, and $K_t$ are the Seebeck coefficient, absolute temperature, electrical resistivity and total thermal conductivity, respectively.

Conventional thermoelectric devices employ bulk materials (i.e., non-superlattice materials) such as bulk bismuth telluride ($Bi_2Te_3$) alloys, for example, as the thermoelectric material used to form the electrical junction. However, these conventional bulk materials exhibit high lattice thermal conductivity, and hence lower figure of merit ZT, and also offer low cooling power density and lower speed of cooling. As a result, conventional thermoelectric devices, and in particular thermoelectric cooling and/or heating actuators, have proven to be unsuccessful in achieving a significantly enhanced figure of merit (ZT) at practical temperatures, e.g., ZT>2 at temperature ranges from about 200 degrees kelvin (K) (e.g., about −73 degrees Celsius (° C.)) to about 400 K (about 127° C.). As a result, attempts to employ conventional thermoelectric devices in certain applications, such as those requiring reduced device packaging that provides an enhanced figure of merit (ZT) at practical temperatures, as well as high cooling power density and higher cooling speed, have been unsuccessful in the past.

Various non-limiting example embodiments described herein include a fast-rate thermoelectric device including thin-film thermoelectric materials capable of significantly enhancing the figure of merit (ZT) of the device, high cooling power density, and faster cooling speeds compared to bulk thermoelectric cooling devices. According to a non-limiting embodiment, the cooling speed of the fast-rate thermoelectric device described herein is inversely proportional to the thickness of the thin-film thermoelectric material (e.g., a squared value of the thin-film thermoelectric material thickness). Accordingly, the increased cooling speed attainable with a TFTE actuator described according to various non-limiting embodiments of the disclosure is essentially as approaches, or even exceeds the speed needed for a human biological cooling response. In this manner, the TFTE actuator according to various non-limiting embodiments of the disclosure can facilitate to thermotactile feasibility in various applications.

Due to the compactness, reduced energy consumption, cooling power density, and speed of the TFTE actuator, future multimodal sensory feedback technologies can integrate pressure-inducing mechanical actuators with one or more thin-film thermoelectric (TE) devices described herein. The pressure-inducing mechanical actuators can also apply a pressure, vibration, and/or other haptic or similar tactile effect. Accordingly, the TFTE actuator can elicit a complex array of thermotactile sensory stimulations.

According to one or more non-limiting embodiments, one or more TFTE actuators described according to various non-limiting embodiments of the disclosure can be utilized to establish a noninvasive thermoneural human-machine interface capable of providing sensations of temperature to a residual (phantom) limb. For example, the TFTE device is capable of providing enhanced perceptual qualities and increased speeds during which thermal sensations can be sensed in humans. Accordingly, one or more fast-rate thin-film thermoelectric (TFTE) devices can be utilized to apply heat pulses and/or cold pulses to regenerate nerve damages, check human responses that have been slowed down due to health issues like stroke, and identify nerve damage.

The results provided by the fast-rate thin-film thermoelectric (TFTE) device according to various non-limiting embodiments described herein have implications for use in human-machine interfaces and other areas such as, for example, immersive mixed reality, wearables, mapping thermal-mediated neural circuits, diagnosing sensory symptoms after stroke, and advanced wound care. In one example embodiment, a fast-rate thermoelectric device used in an interactive reality device such as, for example, provide thermal sensations in a virtual reality (VR) device and/or augmented reality (AR) device. The VR/AR device can implement an array of TFTE devices that implement a thin-film thermoelectric material having a thickness ranging, for example, from about 5 microns to 25 microns. In some non-limiting embodiments, a thinner material can be implemented to provide increased cooling speeds of thermal sensations in a wearable haptic device.

Conventional VR/AR devices are typically operate based on touch and/or pressure sensing. Combining fast-acting thermal modalities with the TFTE devices, described herein can facilitate VR/AR devices that provide a much richer and enhanced multi-modal experience (e.g., pressure, temperature, etc.). For example, adding a sense of temperature, along with pressure, would increase modalities by more than a factor of 5 (e.g., only tactile, only cooling, cooling and tactile simultaneously, only heating, and heating and tactile simultaneously etc.). Also, combining the range of pressures and range of temperatures, the possibilities for AR/VR modalities can be substantially increased.

The fast-rate thermoelectric (TE) devices described to various non-limiting embodiments may also be attractive for beverage coolers, thereby significantly lowering the energy budget to maintain objects cold over a long time for an anticipated delivery to a customer on demand.

Such fast-rate TFTE devices as described according to various non-limiting embodiments are also relevant for medical applications like cauterization and cryo-surgery.

Such fast rate TFTE devices according to various non-limiting embodiments of the present disclosure can be useful for high-speed thermal management of electronics (e.g., microprocessors, controllers, RF power amplifiers in avionics and satellite systems, etc.) where cooling can be effected on demand.

The TFTE devices described to various non-limiting embodiments describe herein are also applicable for cooling high power laser devices, where they operate in a pulse mode and need cooling only on demand when there is heat dissipation.

In one or more non-limiting embodiments, the thin-film thermoelectric material includes a p-type superlattice material and other embodiments of the superlattice or an n-type superlattice material and other embodiments of the superlattice. In some embodiments, the p-type superlattice material includes bismuth/antimony telluride ($Bi_2Te_3/Sb_2Te_3$) which facilitates improved carrier mobility (e.g., control and transport of phonons and electrons) therein, thereby providing a more efficient fast-rate thermoelectric actuator having enhanced figure of merit (ZT)>2 (i.e., ZT=~2) near 300K (about 27° C.), or in some examples even higher, e.g., ZT=~2.4.

In other example (non-limiting) embodiments, the p-type superlattice material or the n-type superlattice material is a controlled hierarchical engineered superlattice structure (CHESS), referred to herein as a "CHESS structure." These CHESS structures can be formed having superlattice periods of varying thicknesses and associated layers of varying thicknesses, in a controllable and reliable format, to obtain a structure that scatters a range of phonons. In this manner, a fast-rate thermoelectric actuator employing a CHESS structure as the thin-film thermoelectric material can further enhance the figure of merit (ZT) to be significantly greater than 2, e.g., about 2.8 (i.e., ZT=~2.8) near 300K (about 27° C.). Thus the thin-film CHESS based actuators could be more energy efficient than thin-film actuators based on superlattices.

In one or more non-limiting embodiments, a fast-rate thermoelectric device includes an array of individual fast-rate thermoelectric actuators. Each thermoelectric device includes a p-n couple and several such p-n couples are connected in series to act in unison to provide thermal actuation. The individual fast-rate thermoelectric actuators are disposed, e.g., are formed, on a wafer and are connected electrically in series with one another, but thermally parallel. A voltage potential can be applied across the array so as to induce an electrical flow through the individual fast-rate thermoelectric actuators. The current flow induces a rapid thermal response (e.g., a rapid heating effect or rapid cooling effect) that is produced from the surface of the fast-rate thermoelectric device. In one or more non-limiting embodiments, the fast-rate thermoelectric device is configured for placement directly against a surface including, but not limited to, skin (e.g., human skin). Accordingly, the rapid-thermal response is quickly applied to the surface in time scales that are consistent with human biological response needs, in response to current flowing through individual fast-rate thermoelectric actuators. In this manner, the fast-rate thermoelectric device can rapidly convey changes in thermal sensation to individuals through contact with the skin for many applications including, but not limited to, biomedical thermotactile applications. It is worth noting that this above array can also be a series-parallel configuration, thereby able to utilize a variety of current and voltage inputs. For example, a 12-couple array can be a 3-by-4 (3×4), or 2×6, or 4×3, etc., where, in the 3×4 array, 3 couples are electrically in series with each other, and 4 such 3-couple strings are electrically in parallel with each other.

Turning now to FIG. 1, a thermoelectric actuator, which in one or more example embodiments is a thin-film thermoelectric (TFTE) actuator 100, is shown. The TFTE actuator 100 includes a backplate 102, a p-leg 104 (e.g., a positive voltage terminal), an n-leg 106 (e.g., a negative voltage terminal), and a p-n couple 108. The backplate 102 can have a thickness ranging, for example, from about 0.5 millimeters (mm) to about 50 micrometers (μm) and can be formed from various thermally conductive materials. In an example embodiment, the backplate 102 may include, or be, a wafer, described in greater detail below with respect to FIG. 2, though alternative embodiments are neither limited nor restricted thereto. In one or more non-limiting, example embodiments, the thermally conductive material of the backplate 102 includes aluminum nitride (Alun). A thermally conductive interface 103 may also be included, which enhances thermal conductivity between the backplate 102 and the p-leg 104 and/or the n-leg 106. It will be appreciated, however, that the thermally conductive interface 103 can be omitted without departing from the spirit or scope of the example embodiments described herein.

In the example embodiment shown in FIG. 1, the p-leg 104 and the n-leg 106 are disposed on, e.g., are formed on, the thermally conductive interface 103. The p-leg 104 and the n-leg 106 are each formed from an electrically conductive material. In one or more non-limiting embodiments, each of the p-leg 104 and the n-leg 106 are formed as separated arrangements of thermally conductive layers. As shown in FIG. 1, for example, an opposing pair of lower conductive layers 110, each corresponding to a respective one of the p-leg 104 and the n-leg 106, is disposed, e.g., is formed, on the surface of the thermally conductive interface 103. An electrically conductive enhancing layer 112 is disposed, e.g., is formed, on the upper surface of each lower conductive layer 110. The electrically conductive enhancing layer 112 has a lower electrical resistance than the lower conductive layer 110, to improve the electrical conductivity between the p-leg 104 and the n-leg 106 and the p-n couple 108. In one or more non-limiting embodiments, the lower conductive layer 110 is formed, for example, from copper (Cu), while the electrically conductive enhancing layer 112 is formed from gold (Au). It will be appreciated, however, that the usage of copper and gold to form the p-leg 104 and n-leg 106 is only one example, and that combinations of other electrically conductive materials can be employed to form the p-leg 104 and the n-leg 106 without departing from the spirit or scope of the example embodiments described herein.

The p-n couple 108 includes one or more p-type TFTE elements 114, one or more n-type TFTE elements 116, a thermally conductive layer 118, and a contact header 120. The p-type TFTE elements 114 include a first end that is disposed (e.g., formed) on a bottom surface (as viewed in FIG. 1) of the thermally conductive layer 118 and an opposing second end configured to contact the p-leg 104. An ohmic contact can be established between the p-type TFTE elements 114 and the p-leg 104 using, for example, an electrically conductive element 122 (e.g., a contact pad or solder bump) including a low-resistance ohmic material such as, for example, indium (In). In at least one non-limiting embodiment, the p-type TFTE element 114 includes a p-type $Bi_2Te/Sb_2Te_3$ superlattice thermoelectric material, which facilitates improved carrier mobility (e.g., control and transport of phonons and electrons) therein. Although the p-n couple 108 is illustrated in FIG. 1 as having two p-type TFTE elements 114, it will be appreciated that less (e.g., one) or additional (e.g., more than two) TFTE elements 114 can be employed without departing from the spirit or scope of the example embodiments described herein. Similarly, the n-type TFTE elements 116 include a first end that is disposed (e.g., formed) on a bottom surface of the thermally conductive layer 118 and an opposing second end configured to contact the n-leg 106. An ohmic contact (e.g., another electrically conductive element 122) can be disposed between the n-type TFTE elements 116 and the n-leg 106 using, for example, a contact pad or solder bump including a low-resistance ohmic material such as, for example, indium (In). In at least one non-limiting embodiment, the n-type TFTE element 116 includes an n-type $Bi_2Te_3/Bi_2Se_3/Bi_2Se_xTe_{3-x}$ superlattice thermoelectric material, which facilitates improved carrier mobility (e.g., control and transport of holes) therein. Although the p-n couple 108 is illustrated as having two n-type TFTE elements 116, it will be appreciated that less (e.g., one) or additional (e.g., more than two) TFTE elements 116 can be employed without departing from the spirit or scope of the example embodiments described herein.

In one or more non-limiting embodiments, the p-type TFTE elements 114 and the n-type TFTE elements 116 are each formed of a superlattice thermoelectric material including a CHESS structure, as described in U.S. patent application Ser. No. 15/700,263, "Superlattice Structures for Thermoelectric Devices," filed Sep. 11, 2017, and published as U.S. Pat. Publication No. 2018/0138106, which are hereby incorporated by reference in their entireties. In at least one non-limiting embodiment, the p-type TFTE elements 114 include a p-type superlattice structure including $Bi_2Te_3/Sb_2Te_3$ and the n-type TFTE elements 116 include an n-type superlattice structure including $Bi_2Te_3/Bi_2Se_3$. As described herein, a CHESS structure can include superlattice periods of varying thicknesses and associated layers of varying thicknesses, in a controllable and reliable format, to obtain a structure that scatters a range of phonons. In this manner, the TFTE actuator 100 can operate as a fast-rate thermoelectric actuator 100 having an enhanced figure of merit (ZT) that is greater than about 2.8 (i.e., ZT=~2.8) near 300K (about 27° C.).

The p-n couple 108 operates according to the Peltier effect to directly convert an electric power input into a temperature differential to generate a heating effect and/or a cooling effect. For instance, the p-n couple 108 establishes a p-n junction between the p-type TFTE elements 114 and the n-type TFTE elements 116. Applying a negative polarity voltage (V−) to the p-leg 104 and a positive polarity voltage (V+) to the n-leg 106 generates a voltage potential, which induces a current flow from n-leg 106, through the p-n couple 108 and to the p-leg 104. The current flow from the n-leg 106 to the p-leg 104 induces cooling at the thermally conductive layer 118 and produces a cooling effect at the thermally conductive layer 118, while rejecting heat toward the p-leg 104 and the n-leg 106. The cooling is transferred to the contact header 120 where a thermotactile effect occurs, while the heat is indirectly transferred to the backplate 102. Accordingly, a surface (e.g., human skin) in contact with the contact header 120 can realize the thermotactile effect (e.g., the cooling effect).

Similarly, a heating effect is produced in response to causing current to flow in the opposite direction described above. Specifically, for example, applying a positive polarity voltage (V+) to the p-leg 104 and a negative polarity voltage (V−) to the n-leg 106 generates a voltage potential that induces a current flow in the opposite direction, i.e., from p-leg 104, through the p-n couple 108 and to the n-leg 106. In this scenario, the current flow from the p-leg 104 to the n-leg 106 induces heating at the thermally conductive layer 118, while rejecting heat, i.e., cooling, thereby lowering temperatures at/toward the p-leg 104 and the n-leg 106. The heat from the thermally conductive layer 118 is transferred to the contact header 120 where a heating thermotactile effect occurs, while the cooling is indirectly transferred to the backplate 102. Accordingly, a surface (e.g., human skin) in contact with the contact header 120 can realize the heating thermotactile effect.

Figure 2:
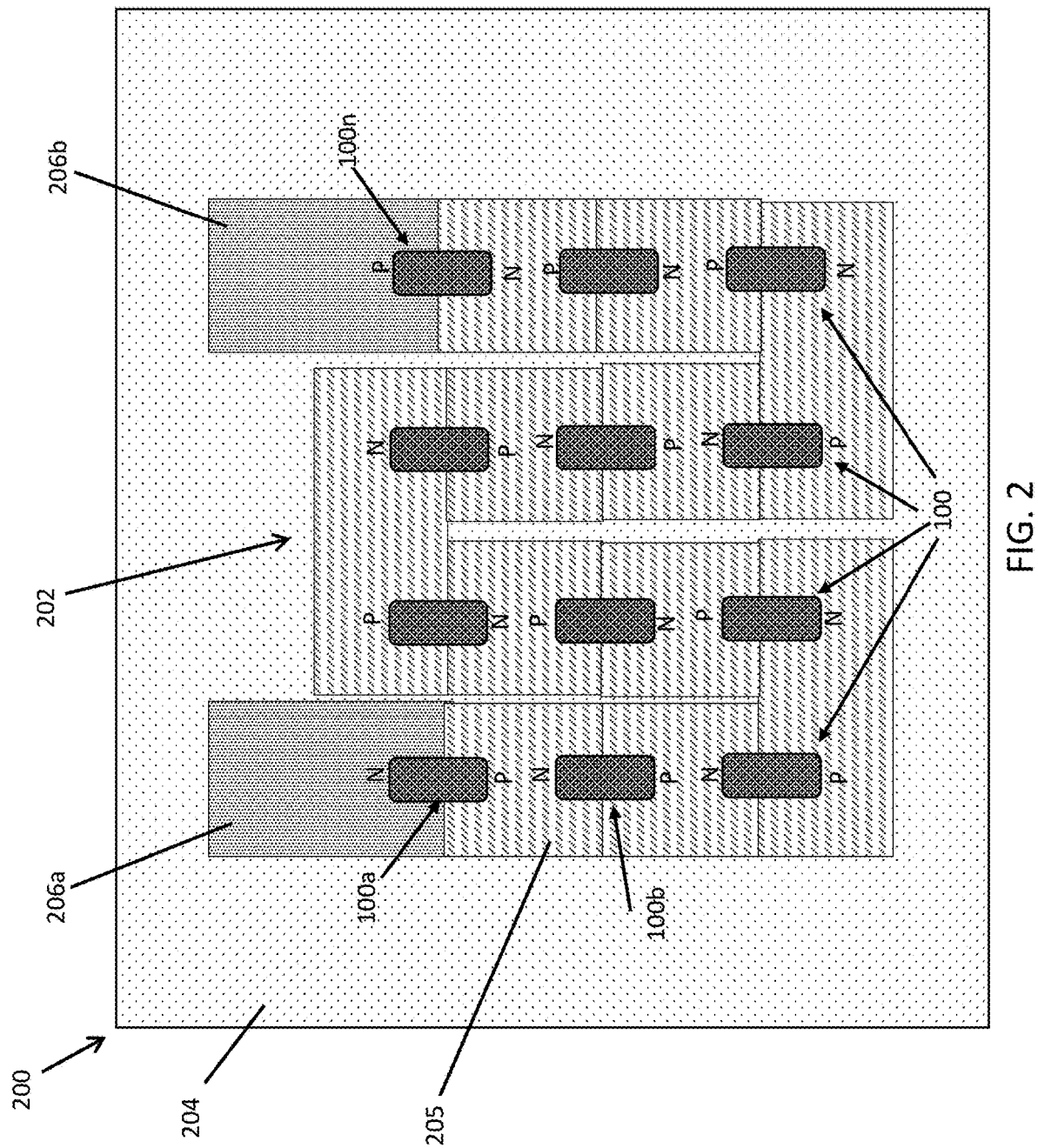
FIG. 2 is a block diagram illustrating a fast-rate thermoelectric device including a plurality of thermoelectric actuators according to a non-limiting embodiment.

Turning now to FIG. 2, a fast-rate thermoelectric device 200 is illustrated according to a non-limiting embodiment. The fast-rate thermoelectric device 200 includes a thermoelectric actuator array 202 disposed, e.g., formed, on a wafer 204. The thermoelectric actuator array 202 includes a plurality of the TFTE actuators 100 (FIG. 1) configured to generate one or both of a heating effect and a cooling effect in response to an electrical current (I). The TFTE actuators 100 are described in greater detail above with reference to FIG. 1.

In at least one non-limiting embodiment, the thermoelectric actuator array 202 includes a plurality of the thin-film thermoelectric (TFTE) actuators 100 disposed/formed on an electrically conductive trace 205 such that the thin-film thermoelectric (TFTE) actuators 100 are connected in electrical series with one another. The electrically conductive trace 205 can be formed of various metals including, but not limited to, copper (Cu), silver (Ag), gold (Au), tin (Sn), aluminum (Al), or combinations thereof. Although the thermoelectric actuator array 202 is illustrated FIG. 2 as being arranged in a 3-by-4 (3×4) matrix or array, i.e., 3 "rows" and 4 "columns" of TFTE actuators 100 (for a total of 12 TFTE actuators 100), additional or alternative example embodiments of the thermoelectric actuator array 202 are not limited thereto and may have smaller or larger array arrangements or designs (e.g., arrays of 2×2, 10×20, 30×10, etc.).

The thermoelectric actuator array 202 according to an example embodiment includes a first power contact node 206a and a second power contact node 206b. The first power contact node 206a is in signal communication with a first TFTE actuator 100a included in the thermoelectric actuator array 202. A second TFTE actuator 100b is connected to the first TFTE actuator 100a via the electrically conductive trace 205, and so on along the electrical path created by the electrically conductive trace 205, to a last (n-th) TFTE actuator 100n (not all TFTE actuators 100 are labeled in FIG. 2; note also that, in the case where there are only two TFTE actuators, i.e. where n=2, the second TFTE actuator 100b is the last (n-th) TFTE actuator 100n). The second power contact node 206b is connected to the n-th (last) TFTE actuator 100n included in the thermoelectric actuator array 202. In an example embodiment, the first power contact node 206a is configured to receive a first voltage polarity V+ (i.e., a voltage having a positive polarity V+), while the second power contact node 206b is configured to receive a second voltage polarity V− (i.e., a voltage having a negative polarity V−) or, alternatively, is connected to ground. It will be appreciated that the polarities of the voltages, i.e., the first and second voltage polarities, applied to the first and second power contact nodes 206a and 206b, respectively, can be reversed to reverse the direction of a current (I), as described in greater detail below. Because the TFTE actuators 100 are arranged in series, the alternating orientations (e.g., p-n, p-n, p-n, p-n, etc.) of the p-n coupling beginning at the second power contact node 206b and ending at the first power contact node 206a are maintained throughout the length of the electrically conductive trace 205, as shown in FIG. 2, denoted by the letter "P" or "N," as appropriate, at each end of a given TFTE actuator 100. It will also be appreciated, however, that, in additional example embodiments, the TFTE actuators 100 can be arranged such that the alternating orientations (e.g., p-n, p-n, p-n, p-n, etc.) of the p-n couplings begin at the first power contact node 206a and ending at the second power contact node 206b. In such an arrangement, the letters "N" and "P" for each of the TFTE actuators 100 would be swapped in FIG. 2.

Figure 3:
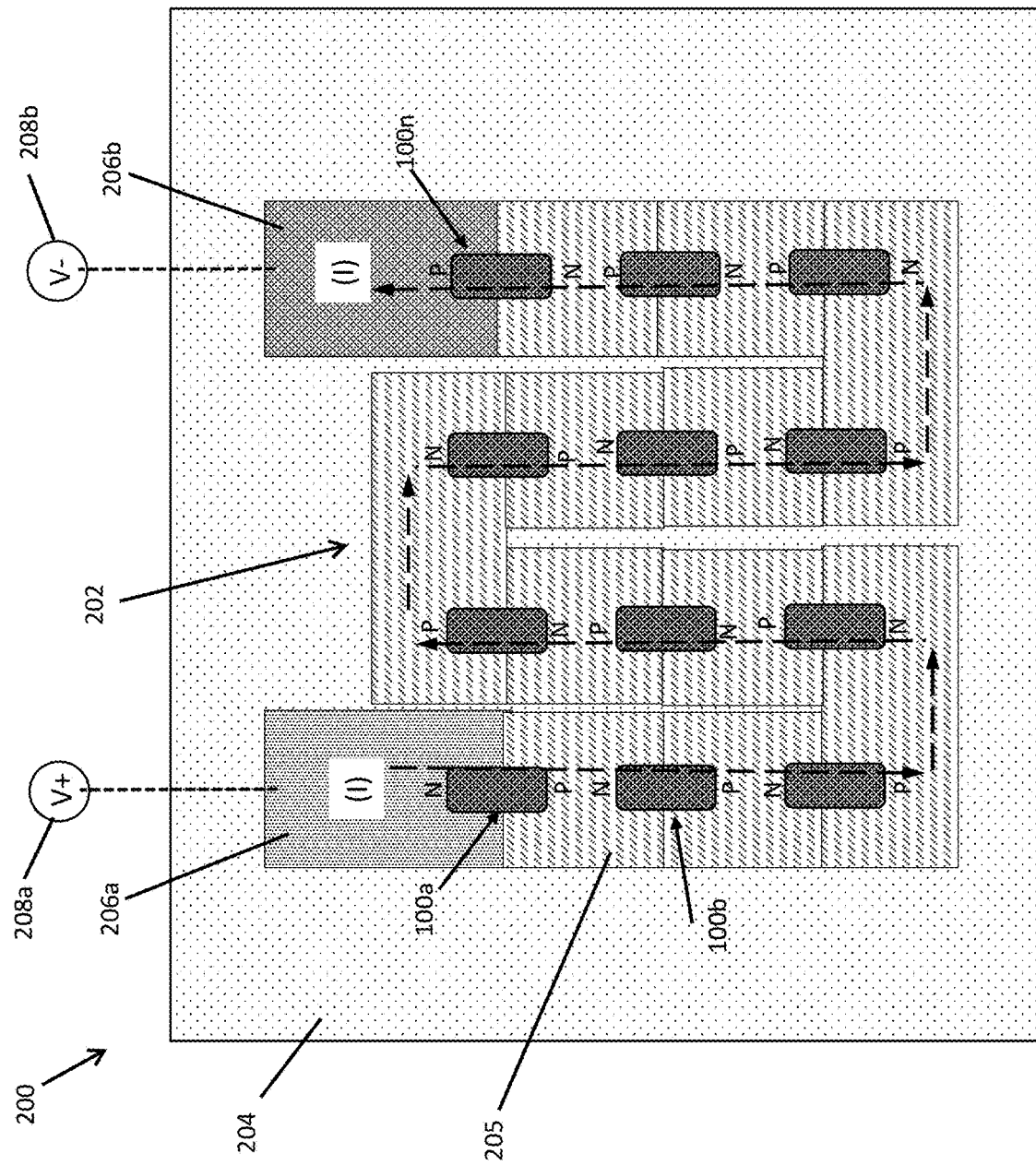
FIG. 3 is a block diagram illustrating a fast-rate thermoelectric device operating in a heating mode according to a non-limiting embodiment.

The fast-rate thermoelectric device 200 is capable of selectively operating in a cooling mode or a heating mode based on a direction of current (I) flowing through the thermoelectric actuator array 202. Referring now to FIG. 3, for example, the fast-rate thermoelectric device 200 is illustrated operating in a cooling mode according to a non-limiting embodiment. The first power contact node 206a is shown connected to a positive voltage source 208a, and thus applies a positive polarity voltage (V+) to the n-type TFTE element (N) of the first TFTE actuator 100a. The second power contact node 206b is shown connected to a negative voltage source 208b, and thus applies a negative polarity voltage (V−) to the p-type TFTE element (P) of the last TFTE actuator 100n. Accordingly, the positive and negative voltage polarities V+ and V− establish a voltage potential across the thermoelectric actuator array 202, which induces an electrical current (I) through the individual TFTE actuators 100 from the first power contact node 206a to the second power contact node 206b. As described in greater detail above, the current (I) flow varies the surface temperature of each thin-film thermoelectric (TFTE) actuator 100 included in the thermoelectric actuator array 202 such that the combination of surface temperatures produces a cooling effect. In an example embodiment, a common contact header (not shown, refer to FIG. 1, described above) can be applied to the upper surface of the TFTE actuators 100. The cooling generated by the TFTE actuators 100 is transferred to the contact header where a thermotactile effect occurs. Accordingly, a surface (e.g., human skin) in contact with the contact header can realize the thermotactile effect (e.g., cooling effect).

Figure 4:
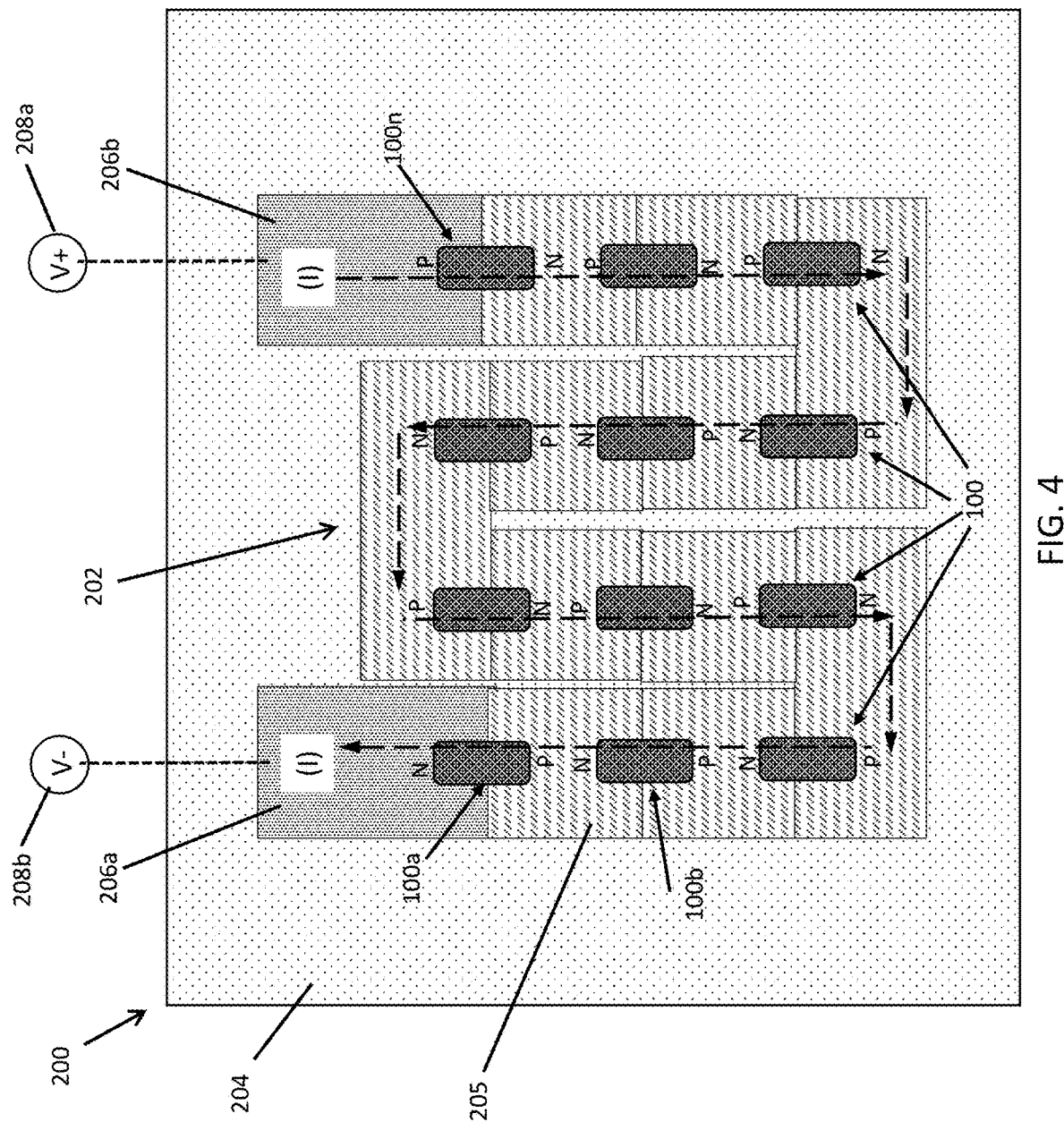
FIG. 4 is a block diagram illustrating a fast-rate thermoelectric device operating in a cooling mode according to a non-limiting embodiment.

Turning now to FIG. 4, the fast-rate thermoelectric device 200 according to an example embodiment is illustrated operating in a heating mode. As shown in FIG. 4, the direction of the flow of the electrical current (I) is opposite that shown in FIG. 3. Specifically, in the heating mode, the second power contact node 206b is connected to a positive voltage source 208a, and thus applies a positive polarity voltage (V+) to the p-type TFTE element (P) of the last TFTE actuator 100n, while the first power contact node 206a is connected to a negative voltage source 208b, and thus applies a negative polarity voltage (V−) to the n-type TFTE element (N) of the first TFTE actuator 100a. Accordingly, the negative and positive voltage polarities V+ and V+, respectively, establish a voltage potential across the thermoelectric actuator array 202, which induces an electrical current (I) through the individual TFTE actuators 100 from the second power contact node 206b to the first power contact node 206a. As described above, the current (I) flow varies the surface temperature of each thin-film thermoelectric (TFTE) actuator 100 included in the thermoelectric actuator array 202 such that the combination of surface temperatures produces a heating effect. In an example embodiment, a common contact header (not shown, refer to FIG. 1, described above) can be applied to the upper surface of the TFTE actuators 100. The heating generated by the TFTE actuators 100 is transferred to the contact header where a thermotactile effect occurs. Accordingly, a surface (e.g., human skin) in contact with the contact header can realize the thermotactile effect (e.g., heating effect). The heating mode is effected in response to the electrical current (I) flowing in the opposite direction from that used to effect the cooling mode (FIG. 3). In one or more non-limiting embodiments, the direction of the current (I) can be selectively controlled by a controller (not shown in FIGS. 3 and 4), which controls a power supply (not shown in FIGS. 3 and 4) that controls and/or includes the positive and negative voltage sources 208a and 208b to respectively provide the first and second voltage polarities V+ and V− to the fast-rate thermoelectric device 200. A controller according to an example embodiment is discussed in greater detail below with reference to FIG. 6.

The fast-rate thermoelectric device 200 represented in the example embodiments described herein offers a substantial and wide range of benefits compared to conventional (bulk) thermoelectric heating and cooling devices. For example, in terms of the cooling effect generated by the cooling mode (FIG. 4), the fast-rate thermoelectric device 200 achieves significantly improved high cooling power density and faster cooling speeds compared to bulk thermoelectric cooling devices. This high cooling power density can be applied not only to electronic applications (e.g., exploited to cool hotspots in microelectronic chips), but also to biological applications (e.g., human thermotactile and thermal perception). These substantially improved device characteristics provide dramatically increased perception in thermotactile applications and human thermal perceptions at a reduced energy budget (i.e., an improved energy efficiency with reduced energy expenditure) in comparison to conventional thermoelectric cooling devices. The fast-rate thermoelectric device 200 according to one or more example embodiments provides similar, substantial benefits and improvements over conventional thermoelectric devices.

Figure 5A:
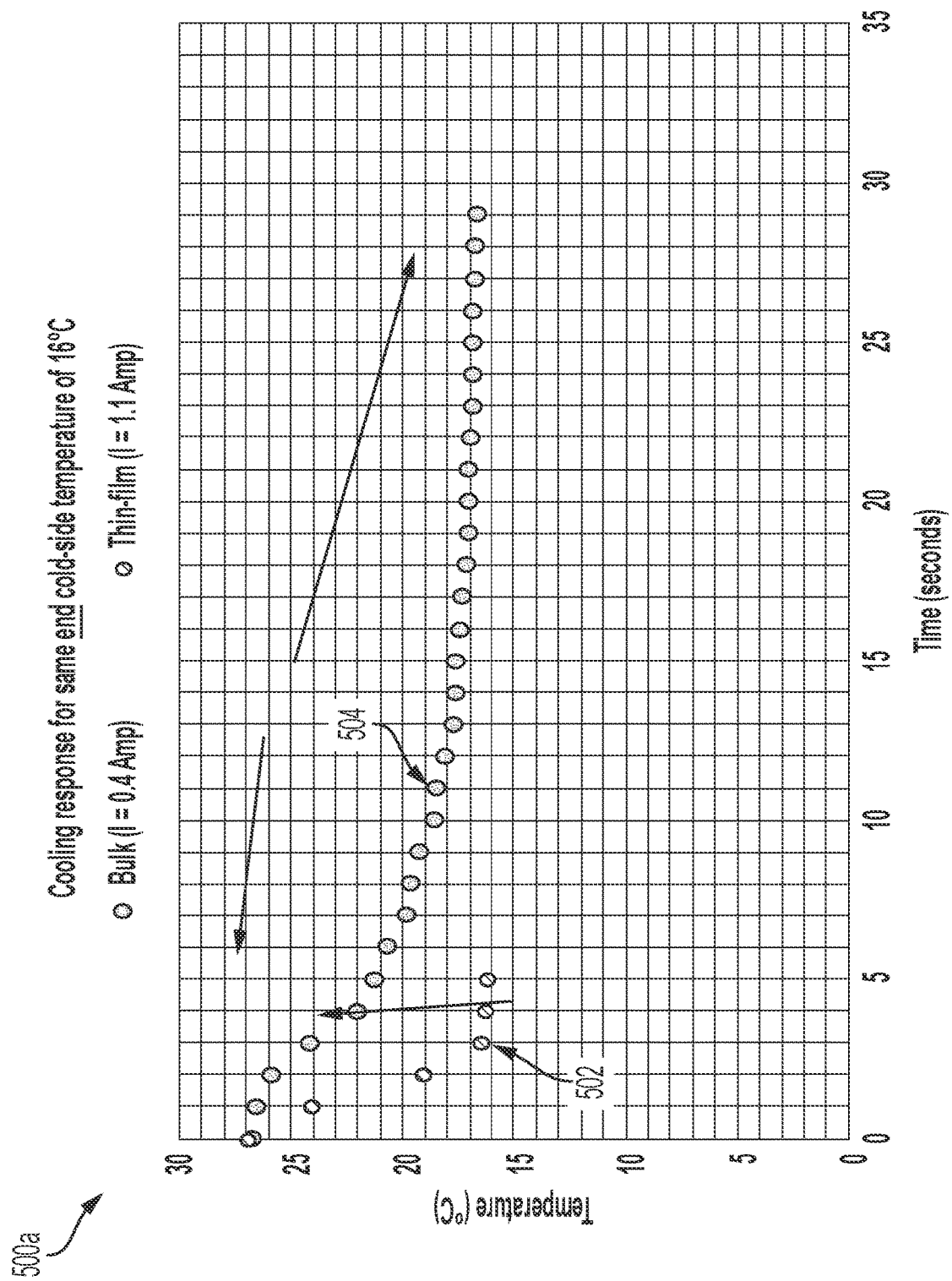
FIG. 5A is a graph of temperature versus time depicting an example of a cooling response of a fast-rate thermoelectric device according to a non-limiting embodiment compared to a cooling response of a conventional thermoelectric cooling device.
Figure 5B:
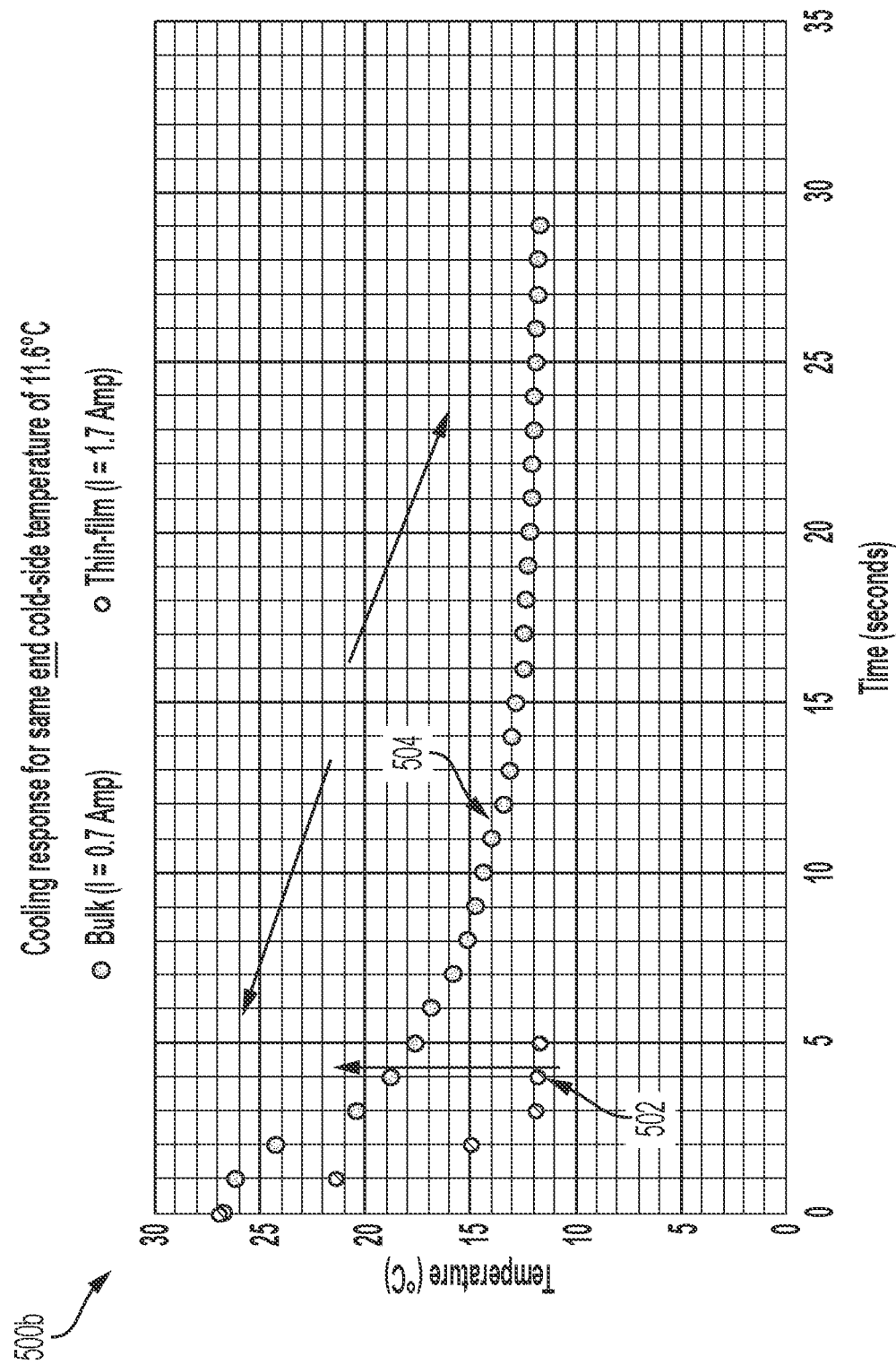
FIG. 5B is a graph of temperature versus time depicting an example of a cooling response of a fast-rate thermoelectric device according to another non-limiting embodiment compared to a cooling response of a conventional thermoelectric cooling device.

Turning to FIGS. 5A and 5B, graphs 500a and 500b, respectively, illustrate an example of a cooling effect 502 provided by the fast-rate thermoelectric device 200 compared to the cooling effect 504 provided by a conventional thermoelectric cooling device. More specifically, graph 500a illustrates differences, in temperature over time, between the cooling response 502 of the fast-rate thermoelectric device 200 and the cooling response 504 of a conventional thermoelectric cooling device to about 16° C. (about 289 K), while graph 500b illustrates differences between the cooling response 502 of the fast-rate thermoelectric device 200 and the cooling response 504 of a conventional thermoelectric cooling device to about 11.6° C. (about 285 K). As shown in FIGS. 5A and 5B, the fast-rate thermoelectric device 200 achieves a significantly faster cooling response 502 time; specifically, the cooling response 502 of the fast-rate thermoelectric device 200 according to an example embodiment is faster than the cooling response 504 of a conventional thermoelectric cooling device by a factor of approximately 8, i.e., the fast-rate thermoelectric device 200 is 8 times more effective in comparison to a conventional thermoelectric cooling device. In addition to the substantially improved performance of the fast-rate thermoelectric device 200 (nearly 8 times faster than a conventional thermoelectric cooling device), as indicated by the time scale of the fast-rate thermoelectric device 200 cooling effect 502, e.g., reaching a target temperature of about 16° C. (FIG. 5A) or 11.6° C. (FIG. 5B) is achieved in about 3 seconds, which is effectively equivalent to that of a typical thermal response time perceived by humans, while the conventional thermoelectric cooling device takes about 25 seconds to achieve a similar cooling effect. It will be appreciated, however, that the fast-rate thermoelectric device 200 is not limited to the aforementioned cooling response, and it will be appreciated that the fast-rate thermoelectric device 200 is capable of achieving even faster cooling response times such as, for example, about 300 hundred milliseconds, or even less. Also, it will be noted that, while cooling response times have been shown and described with reference to FIGS. 5A and 5B, that benefits and improvements afforded by the fast-rate thermoelectric device 200 are not necessarily limited to cooling, e.g., the fast-rate thermoelectric device 200 is configured to provide both heating and cooling thermotactile responses, as described above with reference to FIGS. 3 and 4, for example.

The improved cooling response time provided by the fast-rate thermoelectric device 200 also has a profound benefit in terms of the energy budget necessary to achieve a targeted thermotactile response, i.e., it provides a significant improvement in energy efficiency. Table 1 and Table 2 below illustrate differences between the power input and energy budget for a typical conventional (bulk) thermoelectric cooling device and the fast-rate thermoelectric device 200. More specifically, Table 1 shows the power input and energy budget for a typical conventional thermoelectric cooling device and for the fast-rate thermoelectric device 200 for achieving a cold-side temperature of 16° C. (FIG. 5A). Table 2 illustrates the power input and energy budget for a typical conventional thermoelectric cooling device and the fast-rate thermoelectric device 200 for achieving a cold-side temperature of 11.6° C. (FIG. 5B).

TABLE 1

| Device | I (Amp) | V (Volts) | Power (Watt) | Response time (Sec) | Energy (Joules) |
|---|---|---|---|---|---|
| Conventional TE Device | 0.4 | 0.23 | 0.092 | 25 | 2.3 |
| Fast-Rate TE Device 200 | 1.1 | 0.3 | 0.33 | 3 | 0.99 |

TABLE 2

| Device | I (Amp) | V (Volts) | Power (Watt) | Response time (Sec) | Energy (Joules) |
|---|---|---|---|---|---|
| Conventional TE Device | 0.7 | 0.42 | 0.3 | 25 | 7.5 |
| Fast-Rate TE Device 200 | 1.7 | 047 | 0.8 | 3 | 2.4 |

As can be seen from Tables 1 and 2, the fast-rate thermoelectric device 200 has the higher power levels associated with it, which is to be expected due to its significantly increased cooling power density relative to conventional thermoelectric cooling devices. However, due to the vastly superior cooling time response provided by the fast-rate thermoelectric device 200, the actual energy budget (defined as the integration of power over the time of current flow) is substantially lower for the fast-rate thermoelectric device 200, despite having slightly higher input power. More particularly, the fast-rate thermoelectric device 200 is about 2.4 to 3.0 times more energy efficient for thermotactile functionality compared to conventional thermoelectric cooling devices, due to the combination of increased cooling speed (improved matching with human thermal response) and increased cooling power density.

Figure 6:
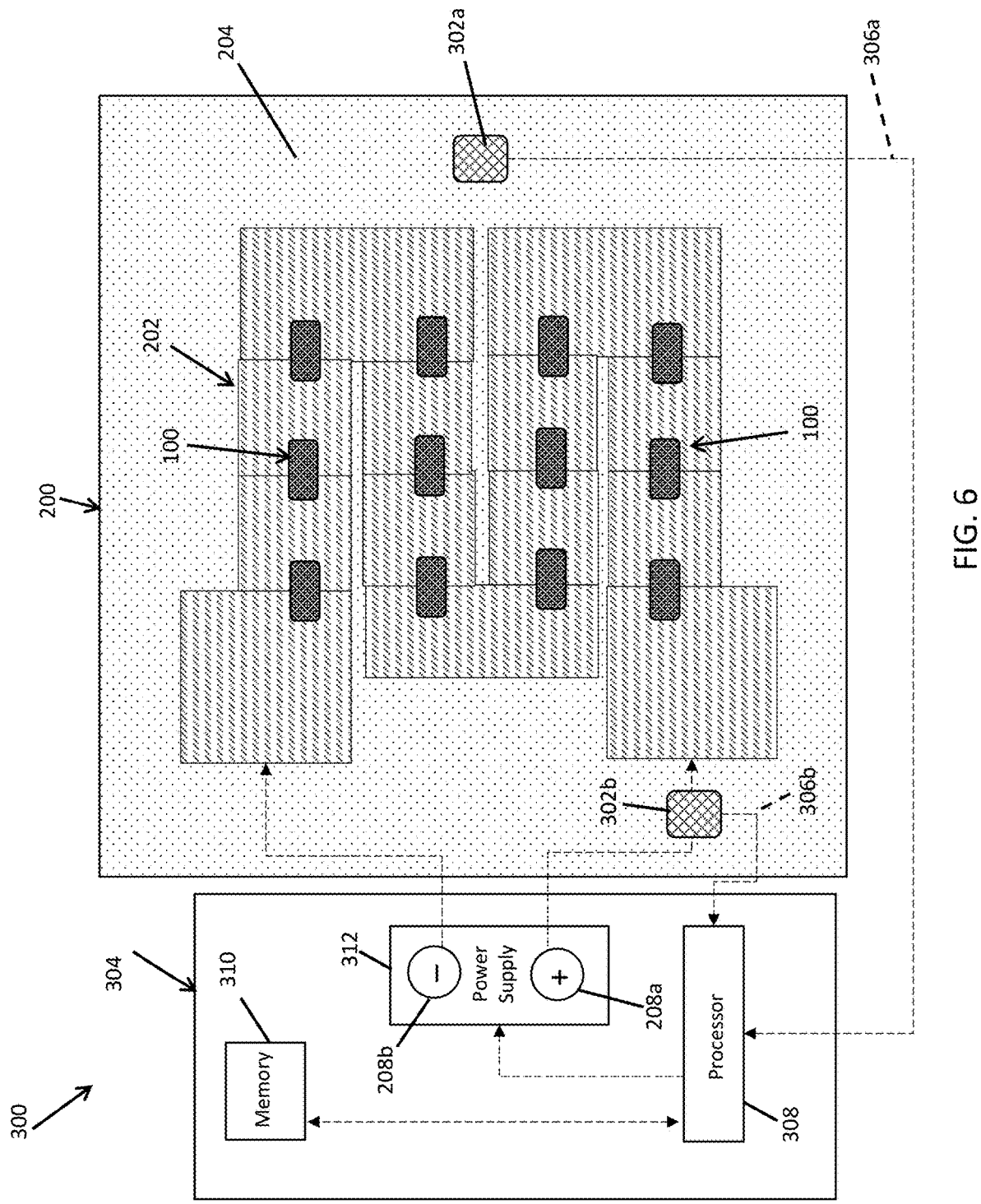
FIG. 6 is a block diagram illustrating a fast-rate thermoelectric device control system according to a non-limiting embodiment.

With reference now to FIG. 6, a fast-rate thermoelectric device control system 300 according to a non-limiting embodiment. The fast-rate thermoelectric device control system 300 includes a controller 304 and one or more sensors 302a, 302b, etc. (for brevity, only two sensors 302 shown in FIG. 6, but additional example embodiments are neither limited nor restricted thereto). The controller 304 is in signal communication with the fast-rate thermoelectric device 200 and the sensor(s) 302, and is configured to control the electrical current (I) described in greater detail above. In one or more non-limiting embodiments, the controller 304 controls the electrical current (I) based at least in part on a feedback signal 306 corresponding to a particular sensor. Specifically, for example, a first sensor 302a can be a temperature sensor disposed or included in the fast-rate thermoelectric device 200, and be configured to measure a temperature associated with one or both of the heating effect and the cooling effect described above and output a first feedback signal 306a indicative of the measured temperature. A second sensor 302b, for example, may be a current sensor disposed or included in the fast-rate thermoelectric device 200, and configured to measure the input current level and output a second feedback signal 306b indicative of the input current level. In either example (or both), the controller 304 can control the fast-rate thermoelectric device 200 to maintain a targeted output temperature, while taking into account surrounding environmental temperatures and/or a temperature of a surface (e.g., human skin) on which the fast-rate thermoelectric device 200 is disposed.

In one or more non-limiting embodiments, the controller 304 includes a processor 308, a memory 310, and a power supply 312. The processor 308 is configured to execute algorithms and computer-readable program instructions stored in the memory 310. The power supply 312 generates voltages, such as the first voltage polarity V+ (a voltage having a positive polarity V+) and the second voltage polarity V− (a voltage having a negative polarity V− or ground), which can be applied to the fast-rate thermoelectric device 200 to induce the electrical current (I), as described in greater detail above and, to that end, may include, incorporate, or instantiate the positive voltage source 208a and the negative voltage source 208b.

The processor 308 is configured to selectively switch the power supply 312 on and off, vary the voltage level to control the level of the electrical current (I) flowing through the fast-rate thermoelectric device 200 and/or change the polarity of the voltage (e.g., from V+ to V− and vice versa) to change the direction of the electrical current (I) flowing through the fast-rate thermoelectric device 200. In at least one embodiment, the processor 308 selects a first voltage polarity that applies a first voltage potential across the thermoelectric actuator array 202. Accordingly, the electrical current flows through the thermoelectric actuator array 202 in a first direction to invoke the cooling mode of the fast-rate thermoelectric device 200, as described in greater detail above with reference to FIG. 3. Further, the processor 308 can dynamically select a second voltage polarity (e.g., an opposite polarity to that of the first voltage polarity) that applies a second voltage potential across the thermoelectric actuator array 202 and thus invokes the heating mode of the fast-rate thermoelectric device 200 (discussed above with respect to FIG. 4). Selection of the voltage polarities can be in response to artificial intelligence operations, machine learning algorithms, and/or manual inputs from a user, although alternative example embodiments are not limited thereto.

The processor 308 is further configured to control the power supply 312 and/or vary the voltage level based on the measured temperature indicated by the feedback signal 306. In one or more embodiments, the processor 308 is configured to determine a target temperature, compare the measured temperature to the target temperature and control the power supply 312 and/or vary the voltage level based on the comparison. The target temperature can be selected or input to the processor 308 by a user, for example. The processor 308 can continuously perform the comparison and actively controls the power supply 312 so as to maintain the measured temperature at the target temperature.

Figure 7:
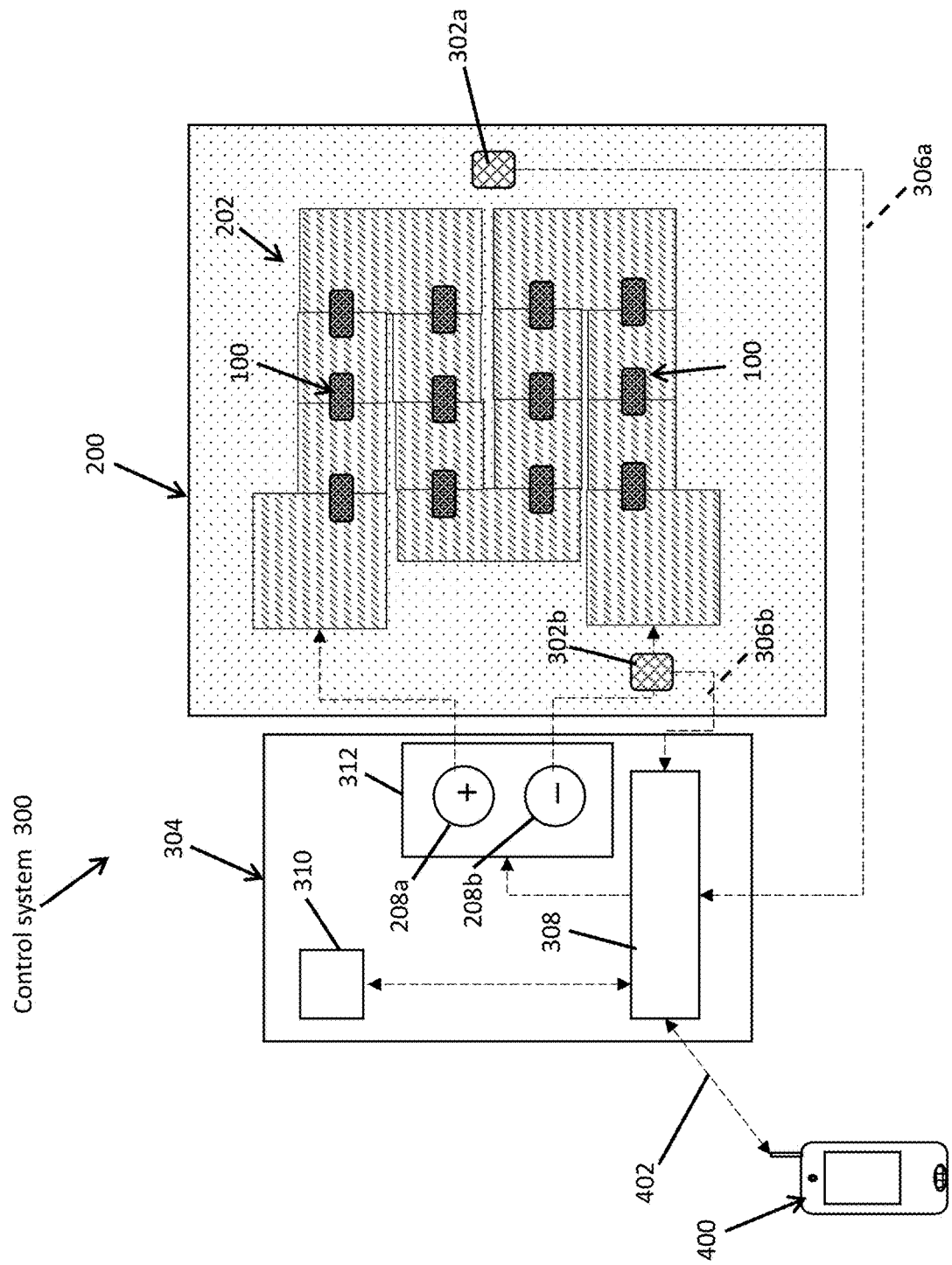
FIG. 7 is a block diagram illustrating a fast-rate thermoelectric device control system configured to exchange data wirelessly according to a non-limiting embodiment.

In one or more non-limiting embodiments, the fast-rate thermoelectric device control system 300 is configured to wirelessly exchanging data. As shown in FIG. 7, for example, the controller 304 is configured to wirelessly communicate with one or more mobile terminal devices 400. In this manner, the controller 304 and mobile terminal device(s) 400 can exchange one or more data signals 402 therebetween. The mobile terminal device 400 can include, but is not limited to, a laptop computer, computer tablet, smartphone, and smart wearable device. The data signals 402 indicate various types of information and data including, but not limited to, external environmental temperatures, weather data, the measured temperature indicated by the feedback signal, power commands for controlling the electrical current, target thermoelectric device temperatures, and temperature profiles.

In one or more non-limiting embodiments, the data signal 402 generated by the mobile terminal device 400 commands the controller 304 to control the temperature generated by the fast-rate thermoelectric device 200. In at least one non-limiting embodiment, the controller 304 is configured determine one or more temperature profiles based on various machine learning algorithms performed either locally or by the mobile terminal device 400, which are then exchanged with the controller 304.

Figure 8:
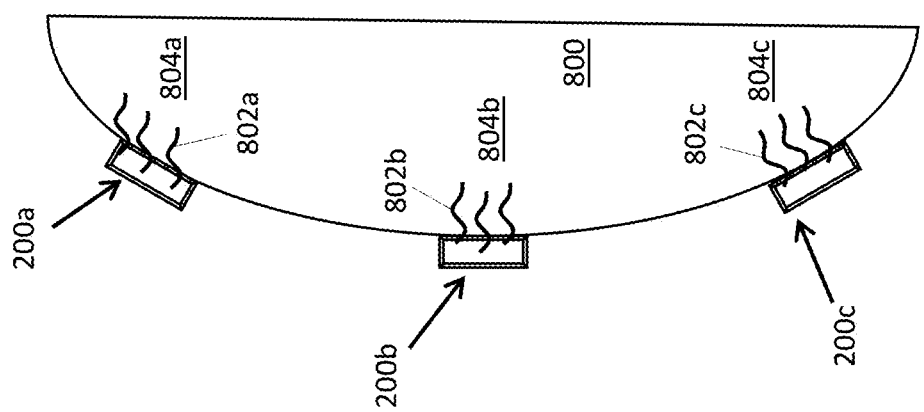
FIG. 8 illustrates a plurality of fast-rate thermoelectric devices disposed against a surface according to a non-limiting embodiment.

Turning now to FIG. 8, a plurality of fast-rate thermoelectric devices 200a, 200b, and 200c are shown disposed against a surface 800. The surface 800 can include, but is not limited to, an electronic device, a semiconductor chip, an integrated circuit component, soft tissue, and human skin (such as, for example, skin on a human limb). Although the fast-rate thermoelectric devices 200a, 200b, and 200c are shown directly contacting an exterior portion of the surface 800, it will be appreciated that one or more of the fast-rate thermoelectric devices 200a, 200b, and 200c can be disposed beneath the surface 800. In scenarios where the surface 800 is human skin, for example, one or more of the fast-rate thermoelectric devices 200a, 200b, and 200c can be disposed beneath the surface 800, e.g., subcutaneously, allowing the fast-rate thermoelectric device to contact soft tissue.

As described herein, the fast-rate thermoelectric devices 200a, 200b, and 200c are configured to apply a thermotactile stimulation 802a, 802b, and 802c, respectively, to the surface 800. The thermal thermotactile stimulations 802a, 802b, and 802c can include, for example, a cooling effect. In one or more non-limiting embodiments, the thermotactile stimulations 802a, 802b, and 802c (e.g., a cooling effect and/or a heating effect) can be applied to and/or penetrate into the surface 800. In example embodiments where the surface includes human skin or a human limb, the penetrating cooling effect and/or the heated effect induces a thermotactile sensation perceived by a human, though alternative example embodiments are not limited thereto, as the thermotactile sensation may also be applied to and perceived by non-humans (other animals), for example. In individuals with limb amputation, for example, one or more fast-rate thermoelectric devices 200a, 200b, and 200c can be disposed against or on one or more locations 804a, 804b, 804c, respectively, on, in, or neat the surface 800 of an amputated site of the residual limb. The generated cooling effect and/or the heating effect can penetrate through the skin and soft tissue of the amputated site and reach functioning free nerve endings subcutaneously. Accordingly, the thermotactile stimulations 802a, 802b, 802c (e.g., a cooling effect) achieved by the fast-rate thermoelectric device 200 provides realistic, real-time, and meaningful thermal information to individuals with limb amputation for creating complex, multimodal sensations in a natural and fully embodied prosthesis, which simply cannot be achieved using conventional thermoelectric cooling devices.

In one or more non-limiting embodiments, a controller (e.g., the controller 304 shown in FIGS. 6 and 7) can synchronize the fast-rate thermoelectric devices 200a, 200b, and 200c for various temporal behaviors. For example, the fast-rate thermoelectric devices 200a, 200b, and 200c can be synchronized to operate in unison, or can operate offset with respect to one another by a set time. The unison and offset operations can be selected by the controller 304, or may be selected manually (by an individuals with a limb amputation, for example).

It will be understood that, although three fast-rate thermoelectric devices 200a, 200b, and 200c are shown in FIG. 8, along with three corresponding respective locations 804a, 804b, 804c, and three corresponding thermotactile stimulations 802a, 802b, 802c, respectively, that alternative example embodiments are neither limited nor restricted thereto, and that any number of fast-rate thermoelectric devices may be provided and disposed accordingly to allow different thermotactile stimulations in different locations.

Figure 9:
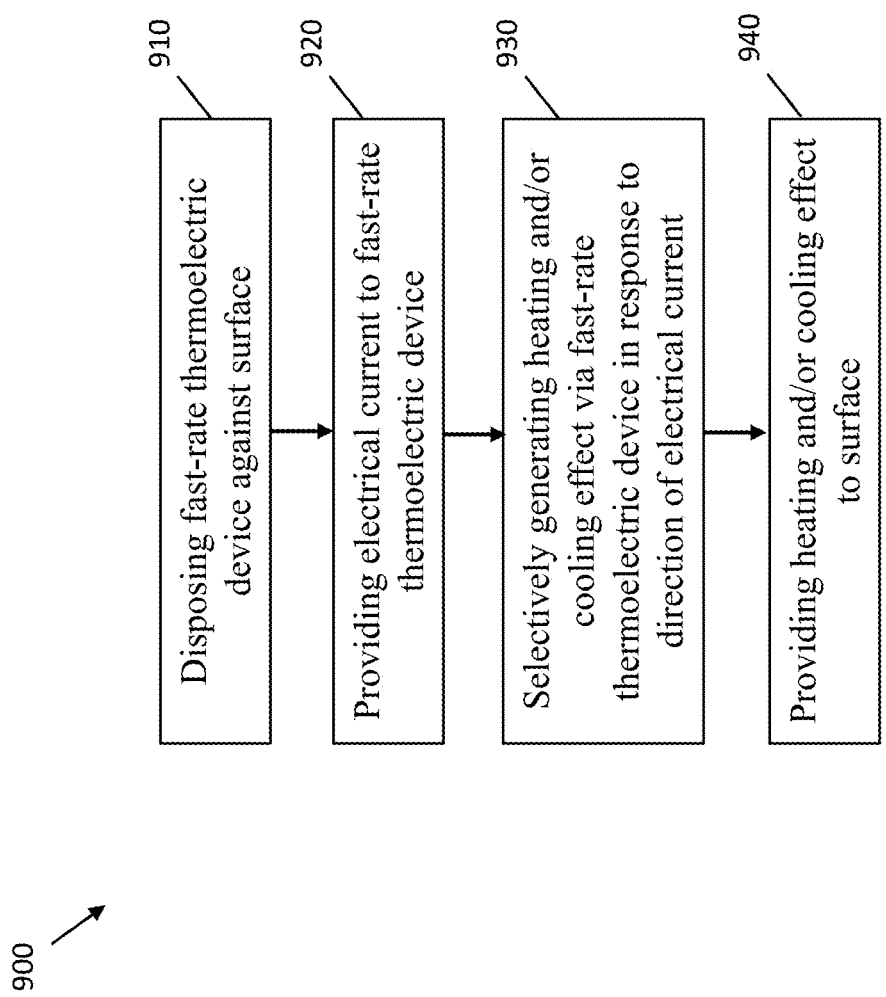
FIG. 9 depicts a method of providing thermotactile stimulation according to a non-limiting embodiment.

One or more non-limiting example embodiments include providing the thermotactile stimulations described above using the fast-rate thermoelectric device 200 shown and described herein, as will now be described in further detail with reference to FIG. 9. As shown in FIG. 9, a method 900 for providing thermotactile stimulation includes, in a first step 910, disposing a fast-rate thermoelectric device against a surface (e.g., human skin). The method 900 further includes providing (e.g., delivering) an electrical current to the fast-rate thermoelectric device (step 920), selectively generating one (or both) of a heating effect and a cooling effect via the fast-rate thermoelectric device, in response to a direction of the electrical current (step 930), and providing (e.g., delivering) the heating effect and/or the cooling effect to the surface (step 940). Additional details of the method 900 (and associated steps 910, 920, 930, and 940) have been shown and described in greater detail herein and, for purposes of brevity, will not be repeated here. It will be understood, however, that additional or alternative example embodiments of providing thermotactile stimulation may include any or all features shown or described herein, and that additional example method embodiments include, for example, manufacturing the devices shown and described herein.

The computer control functionality described herein can be implemented using machine learning and/or natural language processing techniques. In general, machine learning techniques are run on so-called "neural networks," which can be implemented as programmable computers configured to run a set of machine learning algorithms. Neural networks incorporate knowledge from a variety of disciplines, including neurophysiology, cognitive science/psychology, physics (such as statistical mechanics), control theory, computer science, artificial intelligence, statistics/mathematics, pattern recognition, computer vision, parallel processing and hardware (e.g., digital/analog/very large scale integration (VLSI)/optical/etc.).

The basic function of neural networks and their machine learning algorithms is to recognize patterns by interpreting unstructured sensor data through a kind of machine perception. Unstructured real-world data in its native form (e.g., images, sound, text, or time series data) is converted to a numerical form (e.g., a vector having magnitude and direction) that can be understood and manipulated by a computer. The machine learning algorithm performs multiple iterations of learning-based analysis on the real-world data vectors until patterns (or relationships) contained in the real-world data vectors are uncovered and learned. The learned patterns/relationships function as predictive models that can be used to perform a variety of tasks, including, for example, classification (or labeling) of real-world data and clustering of real-world data. Classification tasks often depend on the use of labeled datasets to train the neural network (i.e., the model) to recognize the correlation between labels and data. This is known as supervised learning. Examples of classification tasks include detecting people/faces in images, recognizing facial expressions (e.g., happy, angry, etc.) in an image, identifying objects in images (e.g., stop signs, pedestrians, lane markers, etc.), recognizing gestures in video, detecting voices, detecting voices in audio, identifying particular speakers, transcribing speech into text, and the like. Clustering tasks identify similarities between objects, which are grouped according to those characteristics in common, and which differentiate them from other groups of objects. These groups are known as "clusters."

An example of machine learning techniques that can be used to implement aspects of the example embodiments described herein will be described with reference to FIGS. 10 and 11. Specifically, machine learning models configured and arranged according to example embodiments will be described with reference to FIG. 10. A more detailed implementation of portions of the machine learning models shown in FIG. 10 will be described with reference to FIG. 11. Detailed descriptions of an example computing system and network architecture capable of implementing one or more example embodiments described herein will be provided with reference to FIG. 12.

Figure 10:
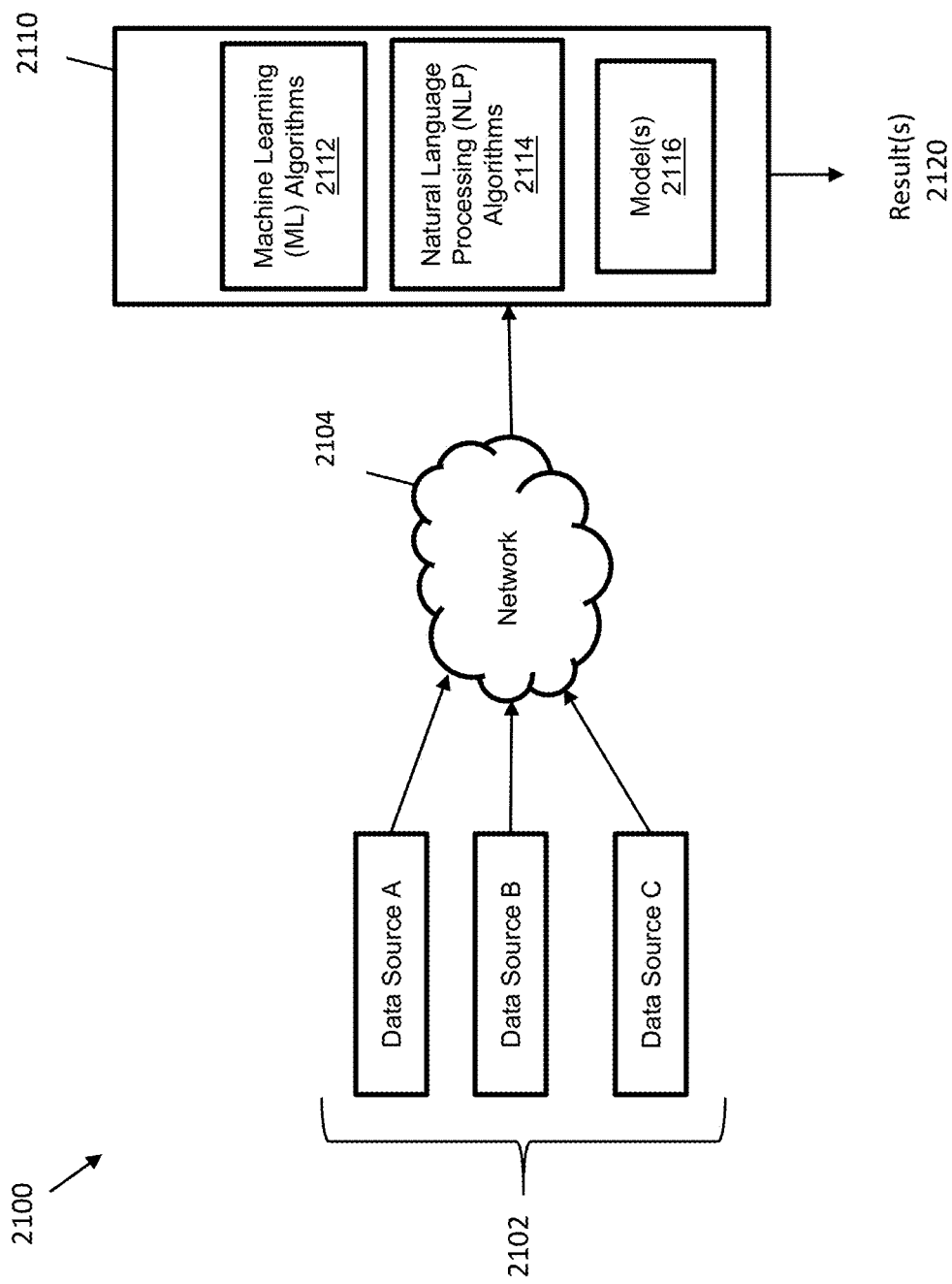
FIG. 10 depicts a classifier system according to a non-limiting embodiment.

FIG. 10 depicts a block diagram showing a classifier system 2100 capable of implementing various aspects of the example embodiments described herein. More specifically, the functionality of the classifier system 2100 is used in example embodiments to generate various models and sub-models that can be used to implement computer functionality in example embodiments described herein. In one example embodiment, the classifier system 2100 includes data sources 2102, e.g., a plurality of data sources 2102 including therein data sources "A," "B," and "C" shown in FIG. 10, in communication through a network 2104 with a classifier 2110. According to some non-limiting embodiments, the data sources 2102 can bypass the network 2104 and feed directly into the classifier 2110, though this is not shown in FIG. 10. The data sources 2102 provide data/information inputs that will be evaluated by the classifier 2110 in accordance with example embodiments. The data sources 2102 also provide data/information inputs that can be used by the classifier 2110 to train and/or update model(s) 2116 created by the classifier 2110. The data sources 2102 can be implemented as a wide variety of data sources, including but not limited to, sensors configured to gather real time data, data repositories (including training data repositories), and outputs from other classifiers. The network 2104 can be any type of communications network, including but not limited to local networks, wide area networks, private networks, the Internet, and the like.

Figure 12:
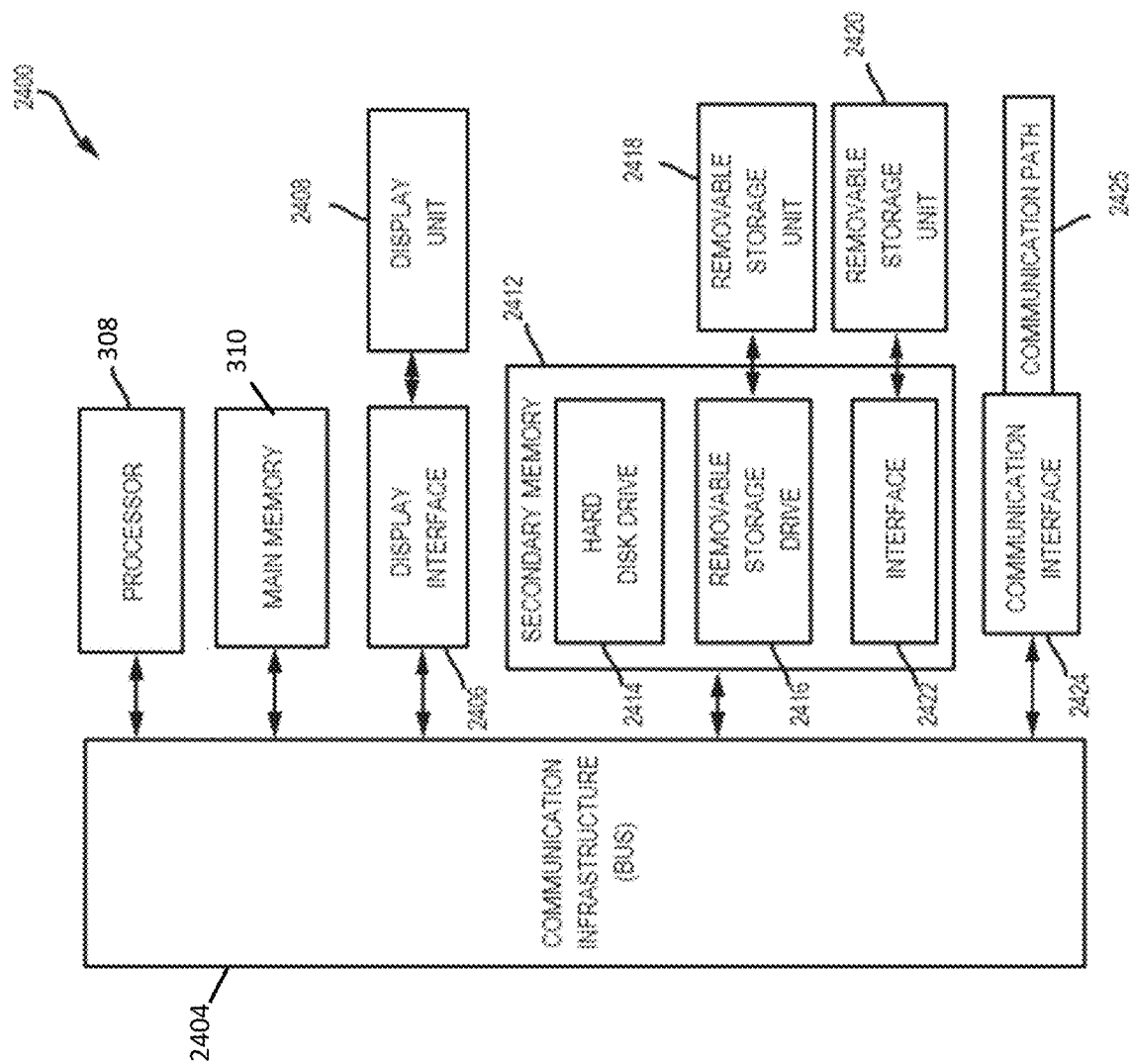
FIG. 12 depicts a computer system according to a non-limiting embodiment.

The classifier 2110 can be implemented as algorithms executed by a programmable computer such as a processing system 2400 (FIG. 12). As shown in FIG. 10, the classifier 2110 includes a suite of machine learning (ML) algorithms 2112, natural language processing (NLP) algorithms 2114, and model(s) 2116 that are relationship (or prediction) algorithms generated (or learned) by the ML algorithms 2112. The algorithms 2112, 2114, 2116 of the classifier 2110 are depicted separately for ease of illustration and explanation. In various example embodiments, the functions performed by the algorithms 2112, 2114, 2116 of the classifier 2110 can be distributed differently than shown in FIG. 10. For example, where the classifier 2110 is configured to perform an overall task having sub-tasks, the suite of ML algorithms 2112 can be segmented such that a portion of the ML algorithms 2112 executes each sub-task, and a portion of the ML algorithms 2112 executes the overall task. Additionally, in some example embodiments, the NLP algorithms 2114 can be integrated within the ML algorithms 2112.

The NLP algorithms 2114 include speech recognition functionality that allows the classifier 2110 and, more specifically, the ML algorithms 2112, to receive natural language data (text and audio) and apply elements of language processing, information retrieval, and machine learning to derive meaning from the natural language inputs and potentially take action based on the derived meaning. The NLP algorithms 2114 used in accordance with example embodiments can also include speech synthesis functionality that allows the classifier 2110 to translate result(s) 2120 outputted from the classifier 2110 into natural language (text and audio) to communicate aspects of the result(s) 2120 as natural language communications.

The NLP and ML algorithms 2114, 2112 receive and evaluate input data (e.g., training data and data-under-analysis) from the data sources 2102. The ML algorithms 2112 include functionality to interpret and utilize data from the data sources 2102 based on a format thereof. For example, where the data sources 2102 include image data, the ML algorithms 2112 can include visual recognition software configured to interpret image data. The ML algorithms 2112 apply machine learning techniques to received training data (e.g., data received from one or more of the data sources 2102) in order to, over time, create/train/update one or more models 2116 that model the overall task and the sub-tasks that the classifier 2110 is designed to complete.

Figure 11:
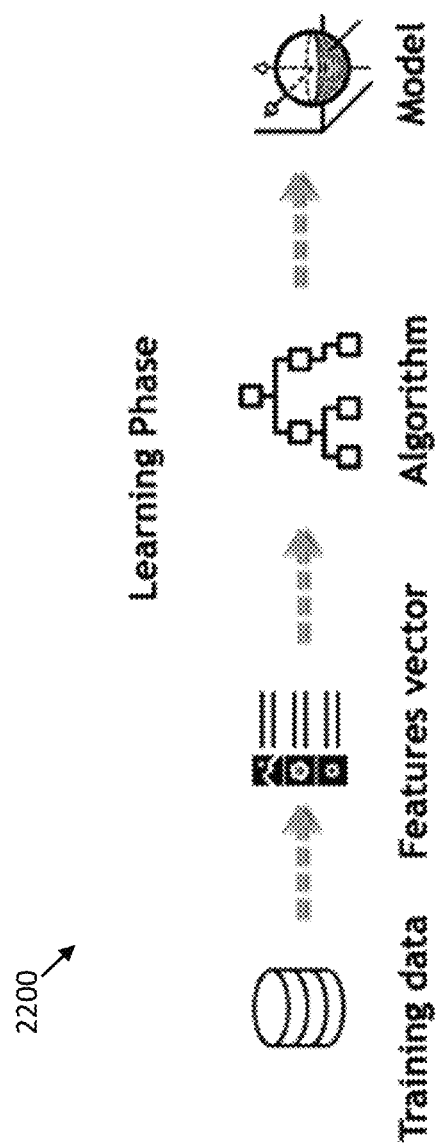
FIG. 11 depicts a learning phase that can be implemented by a classifier system according to a non-limiting embodiment.

Referring now to FIGS. 10 and 11 collectively, FIG. 11 depicts an example of a learning phase 2200 performed by the ML algorithms 2112 to generate the above-described models 2116. In the learning phase 2200, the classifier 2110 extracts features from training data and coverts the features to vector representations that can be recognized and analyzed by the ML algorithms 2112. The features vectors created by the classifier 2110 are analyzed by the ML algorithm 2112 to "classify" the training data against a model, such as a target model (or a particular model's task) and uncover relationships between and among the resulting classified training data. Examples of suitable implementations of the ML algorithms 2112 include but are not limited to neural networks, support vector machines (SVMs), logistic regression, decision trees, hidden Markov Models (HMMs), etc. The learning or training performed by the ML algorithms 2112 can be supervised, unsupervised, or a hybrid that includes aspects of supervised and unsupervised learning. Supervised learning is when training data is already available and classified/labeled. Unsupervised learning is when training data is not classified/labeled so must be developed through iterations of the classifier 2110 and the ML algorithms 2112. Unsupervised learning can utilize additional learning/training methods including, for example, clustering, anomaly detection, neural networks, deep learning, and the like.

When the models 2116 are sufficiently trained by the ML algorithms 2112, the data sources 2102 that generate "real world" data are accessed, and the "real world" data is applied to the models 2116 to generate usable versions of the results 2120. In some example embodiments, the results 2120 can be fed back to the classifier 2110 and used by the ML algorithms 2112 as additional training data for updating and/or refining the models 2116.

According to various non-limiting embodiments, the ML algorithms 2112 and the models 2116 can be configured to apply confidence levels (CLs) to various ones of their results/determinations (including the results 2120) in order to improve the overall accuracy of the particular result/determination. When the ML algorithms 2112 and/or the models 2116 make a determination or generate a result for which the value of a CL is below a predetermined threshold (TH) (i.e., CL<TH), the result/determination can be classified as having sufficiently low "confidence" to justify a conclusion that the determination/result is not valid, and this conclusion can be used to determine when, how, and/or if the determinations/results are handled in downstream processing. In contrast, if CL>TH, the determination/result can be considered valid, and this conclusion can be used to determine when, how, and/or if the determinations/results are handled in downstream processing. Many different predetermined TH levels can be provided. The determinations/results with CL>TH can be ranked from the highest CL>TH to the lowest CL>TH in order to prioritize when, how, and/or if the determinations/results are handled in downstream processing.

Thus, according to various non-limiting embodiments, the classifier 2110 can be configured to apply confidence levels (CLs) to the results 2120. When the classifier 2110 determines that a CL in the results 2120 is below a predetermined threshold (TH) (i.e., CL<TH), the results 2120 can be classified as sufficiently low to justify a classification of "no confidence" in the results 2120. If CL >TH, the results 2120 can be classified as sufficiently high to justify a determination that the results 2120 are valid. Many different predetermined TH levels can be provided such that the results 2120 with CL>TH can be ranked from the highest CL>TH to the lowest CL>TH.

The functions performed by the classifier 2110, and more specifically by the ML algorithm 2112, can be organized as a weighted directed graph, wherein the nodes are artificial neurons (e.g. modeled after neurons of the human brain), and wherein weighted directed edges connect the nodes. The directed graph of the classifier 2110 can be organized such that certain nodes form input layer nodes, certain nodes form hidden layer nodes, and certain nodes form output layer nodes. The input layer nodes couple to the hidden layer nodes, which couple to the output layer nodes. Each node is connected to every node in the adjacent layer by connection pathways, which can be depicted as directional arrows that each has a connection strength. Multiple input layers, multiple hidden layers, and multiple output layers can be provided. When multiple hidden layers are provided, the classifier 2110 can perform unsupervised deep-learning for executing the assigned task(s) of the classifier 2110.

Similar to the functionality of a human brain, each input layer node receives inputs with no connection strength adjustments and no node summations. Each hidden layer node receives its inputs from all input layer nodes according to the connection strengths associated with the relevant connection pathways. A similar connection strength multiplication and node summation is performed for the hidden layer nodes and the output layer nodes.

The weighted directed graph of the classifier 2110 processes data records (e.g., outputs from the data sources 2102) one at a time, and it "learns" by comparing an initially arbitrary classification of the record with the known actual classification of the record. Using a training methodology knows as "back-propagation" (i.e., "backward propagation of errors"), the errors from the initial classification of the first record are fed back into the weighted directed graphs of the classifier 2110 and used to modify the weighted directed graph's weighted connections the second time around, and this feedback process continues for many iterations. In the training phase of a weighted directed graph of the classifier 2110, the correct classification for each record is known, and the output nodes can therefore be assigned "correct" values. For example, a node value of "1" (or 0.9) for the node corresponding to the correct class, and a node value of "0" (or 0.1) for the others. It is thus possible to compare the weighted directed graph's calculated values for the output nodes to these "correct" values, and to calculate an error term for each node (i.e., the "delta" rule). These error terms are then used to adjust the weights in the hidden layers so that in the next iteration the output values will be closer to the "correct" values.

FIG. 12 depicts a high-level block diagram of a computer system 2400, which can be used to implement one or more computer processing operations in accordance with example embodiments. The computer system 2400 includes a communication path 2425, which connects the computer system 2400 to additional systems (not depicted) and can include one or more wide area networks (WANs) and/or local area networks (LANs) such as the Internet, intranet(s), and/or wireless communication network(s). The computer system 2400 and, in one example embodiment, additional systems, are in communication via communication path 2425.

The computer system 2400 includes one or more processors, such as the processor 308 described above with respect to FIG. 6, for example. The processor 308 is connected to a communication infrastructure 2404 (e.g., a communications bus, cross-over bar, or network). The computer system 2400 can include a display interface 2406 that forwards graphics, text, and other data from communication infrastructure 2404, or from a frame buffer (not shown) for display on a display unit 2408. The computer system 2400 also includes a main memory, such as the memory 310 (FIG. 6), which may be random access memory (RAM), and can also include a secondary memory 2412. The secondary memory 2412 can include, for example, a hard disk drive 2414 and/or a removable storage drive 2416, which may be, for example, a floppy disk drive, a magnetic tape drive, or an optical disk drive. The removable storage drive 2416 reads from and/or writes to a removable storage unit 2418, and may be, for example, a floppy disk, a compact disc, a magnetic tape, or an optical disk, flash drive, solid state memory, etc., which is read by and written to by the removable storage drive 2416. As will be appreciated, the removable storage unit 2418 includes a computer readable medium having stored therein computer software and/or data.

In an alternative example embodiment, the secondary memory 2412 can include or interact with other similar means for allowing computer programs or other instructions to be loaded into the computer system. Such means can include, for example, a removable storage unit 2420 and an interface 2422. Examples of such means can include a program package and package interface (such as that found in video game devices), a removable memory chip (such as an erasable programmable read only memory (EPROM), or a programmable read only memory (PROM)) and associated socket, and other removable storage units 2420 and interfaces 2422 in communication to allow software and data to be transferred from the removable storage unit 2420 into the computer system 2400.

The computer system 2400 can also include a communications interface 2424. The communications interface 2424 further allows software and data to be transferred between the computer system 2400 and external devices. Examples of the communications interface 2424 can include a modem, a network interface (such as an Ethernet card), a communications port, or a personal computer (PC) card (e.g., a so-called "PCMCIA" card) and associated slot, etc. Software and data transferred via communications interface 2424 are in the form of signals which can be, for example, electronic, electromagnetic, optical, or using other signals capable of being received by the communications interface 2424. These signals are provided to the communications interface 2424 via a channel, e.g., the communication path 2425. The communication path 2425 carries signals and can be implemented using wire or cable, fiber optics, a phone line, a cellular phone link, a radio frequency (RF) link, and/or other communications channels.

Figure 13:
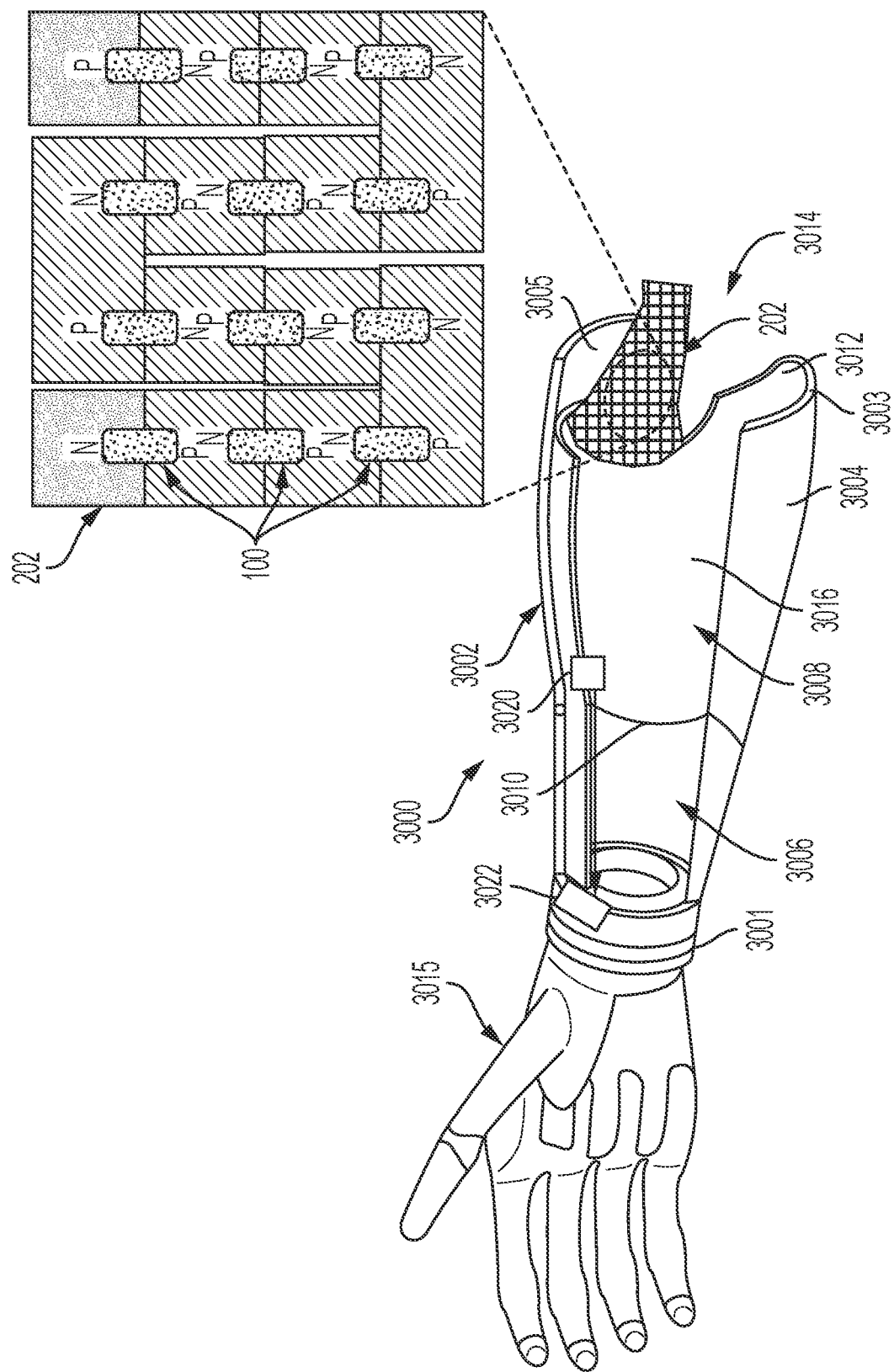
FIG. 13 depicts a thermotactile stimulation prosthesis according to a non-limiting embodiment.
Figure 14:
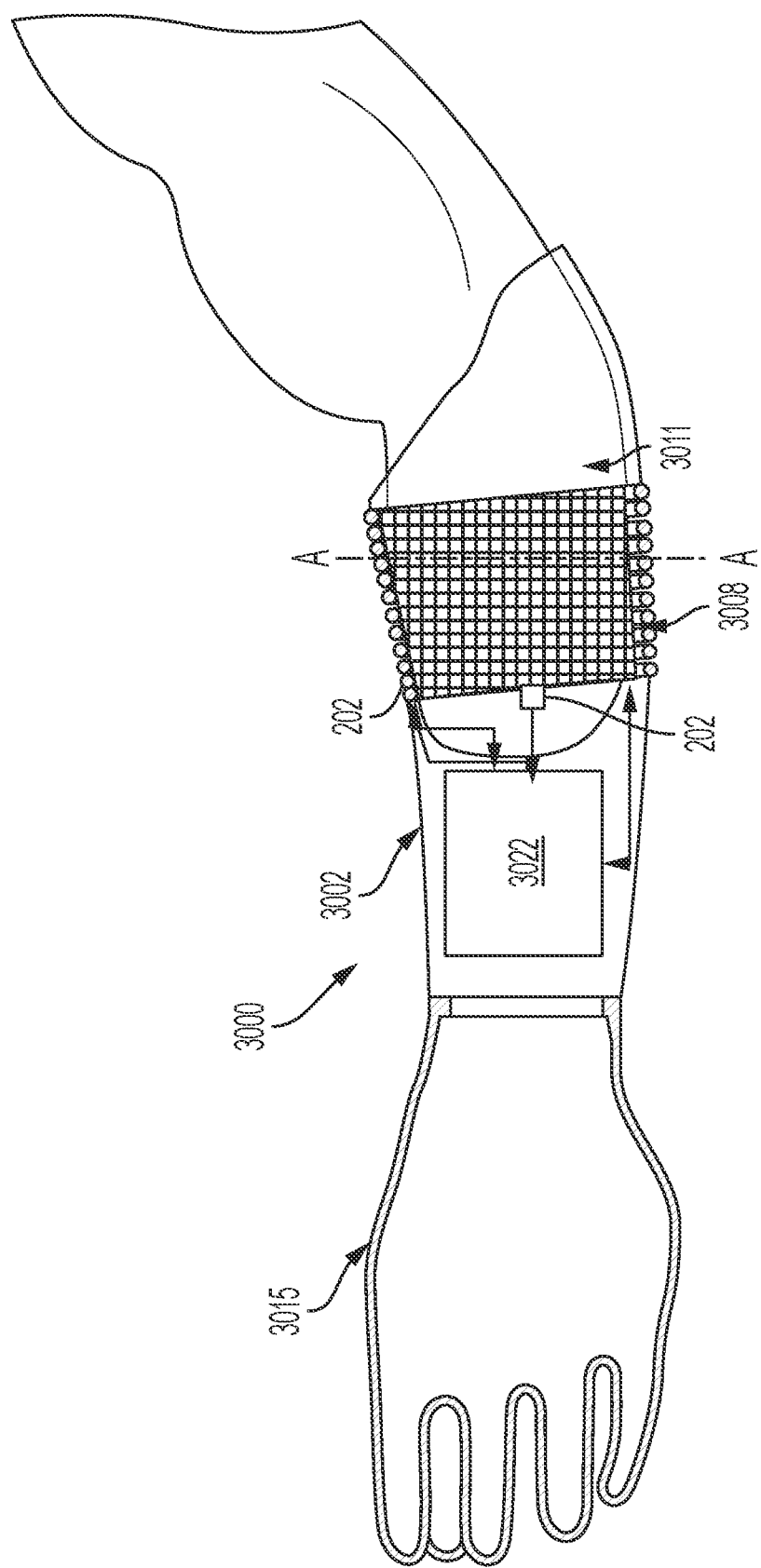
FIG. 14 depicts the thermotactile stimulation prosthesis of FIG. 13 fitted to a human limb according to a non-limiting embodiment.
Figure 15:
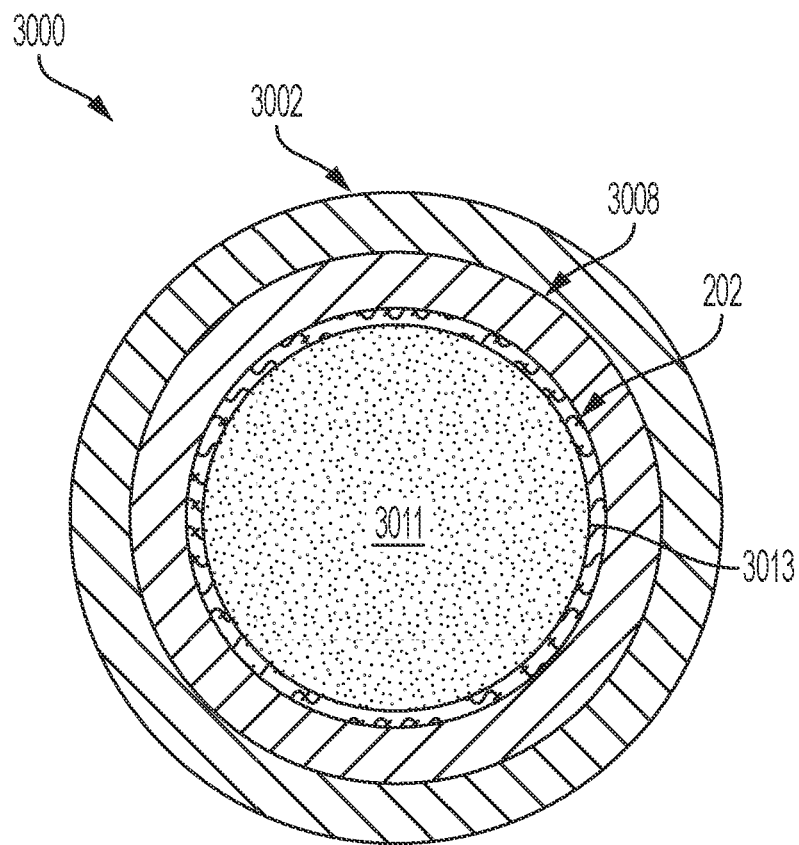
FIG. 15 is a cross-sectional view of the thermotactile stimulation prosthesis of FIG. 14 taken along line A-A.

Turning now to FIGS. 13, 14 and 15, a thermotactile stimulation prosthesis 3000 is illustrated according to a non-limiting embodiment. The thermotactile stimulation prosthesis 3000 can include for example a hollow shell 3002 extending from a distal end 3001 supporting a prosthesis extremity 3015 to a proximate end 3003. The prosthesis extremity 3015 can include but is not limited to a bionic finger, hand, wrist, elbow, forearm, upper arm, foot, leg, knee, or any other body part. The hollow shell 3002 can include an outer shell surface 3004 and an opposing inner shell surface 3005 surrounding an inner void 3006. A socket 3008 is disposed in the inner void 3006. The socket 3008 can extend from a distal end 3010 to a proximate end 3012 that defines an opening 3014 configured to receive a residual limb 3011. The socket 3008 has a socket outer surface 3016 and an opposing socket inner surface 3018 to establish contact with the residual limb 3011. The thermotactile stimulation prosthesis 3000 can include any prosthesis attachment method including a shell 3002 and socket 3008 system. The thermotactile stimulation prosthesis 3000 can also omit the socket 3008 without departing from the scope of the present disclosure. For example, the thermotactile stimulation prosthesis 3000 can include a direct skeletal osseointegration attachment, direct body attachment using tension or compression, or externally mounted sensorized devices where the thermoelectric actuator array 202 is attached to a user's skin.

With continued reference to FIGS. 13, 14 and 15, the thermotactile stimulation prosthesis 3000 further includes a thermoelectric actuator array 202 disposed on the socket inner surface 3018, any other part of the prosthesis that makes contact with the residual limb 3011, or as a standalone actuator array 202 not in contact with the prosthesis and placed on the skin to provide thermotactile sensations. The thermoelectric actuator array 202 is configured to establish a noninvasive thermoneural human-machine interface 3013 between the socket 3008 and the residual limb 3011. The thermoelectric actuator array 202 can also be configured to establish a noninvasive thermoneural human machine interface 3013 by using a signal from the sensorized prosthesis 3000 for actuation or stimulation of the residual limb 3011. Accordingly, the thermotactile stimulation prosthesis 3000 can provide sensations of temperature to the residual limb. The thermotactile stimulation prosthesis 3000 includes a plurality of thin-film thermoelectric (TFTE) actuators configured to generate one or both of a heating effect and a cooling effect in response to an electrical current.

According to one or more non-limiting embodiments, the each of the TFTE actuators 100 includes a p-type controlled hierarchical engineered superlattice structure (CHESS), and an n-type CHESS. The p-type CHESS and the n-type CHESS each include a thin-film thermoelectric material having a material thickness. Accordingly, the cooling speed of each of the TFTE actuators is inversely proportional to the material thickness. For example, the cooling speed of each TFTE actuator 100 can be defined as a squared value of the material thickness.

According to one or more non-limiting embodiments, the thermotactile stimulation prosthesis 3000 includes one or more sensors 3020 and one or more controllers 3022. The sensor 3020 is configured to measure a temperature associated with one or both of the heating effect and the cooling effect and to output a feedback signal indicative of the measured temperature. The controller 3022 is in signal communication with the thermoelectric actuator array 202 and the sensor. The controller is configured to control one or more of the TFTE actuators 100 based on the measured temperature indicated by the feedback signal. For example, the controller 3022 can control the electrical current delivered to the thermoelectric actuator array 202 based at least in part on the feedback signal to control one or both of a heating effect and a cooling effect provided to a residual limb 3011. In one or more non-limiting embodiments, the controller 3022 is configured to control one or more of the TFTE actuators 100 to apply one or both of heat pulses and cold pulses to perform one or a combination of regenerate nerve damages, check human responses, and nerve damage identification.

Figure 16:
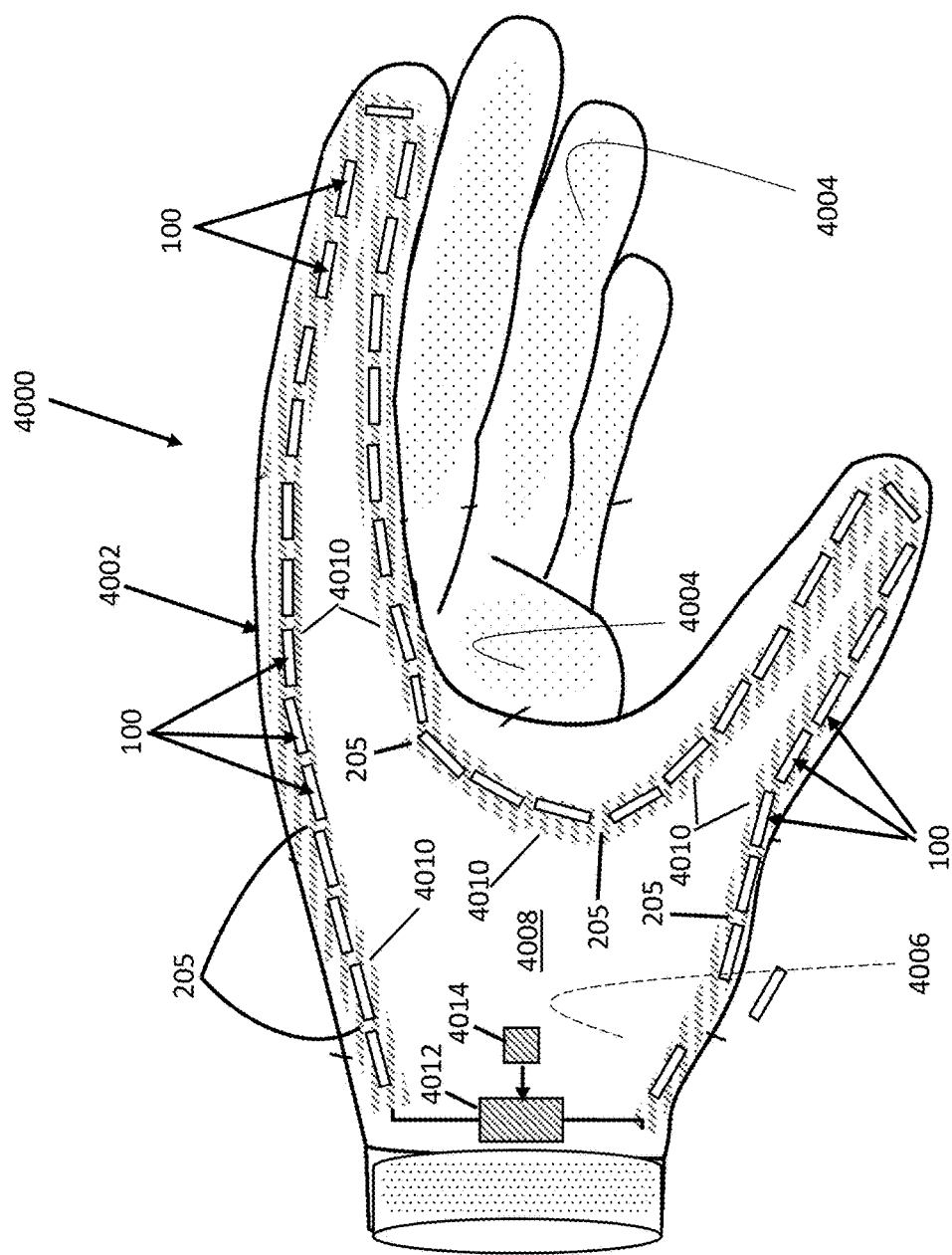
FIG. 16 depicts an interactive reality device according to a non-limiting embodiment of the present disclosure.

With reference now to FIG. 16, an interactive reality device 4000 is illustrated according to a non-limiting embodiment. The interactive reality device 4000 includes a hollow shell 4002 and a plurality of a plurality of thin-film thermoelectric (TFTE) actuators 100. The hollow shell 4002 is configured to fit with a human appendage such as, for example, a hand or a foot. The hollow shell 4002 includes an outer shell surface 4004 and an opposing inner shell surface 4006 surrounding an inner void 4008 configured to receive the human appendage.

The thin-film thermoelectric (TFTE) actuators 100 are disposed on the on the inner shell surface 4006, and are configured to establish a noninvasive thermoneural human-machine interface 4010 capable of providing sensations of temperature to the human appendage or any other part of the human skin. According to a non-limiting embodiment, an electrically conductive trace 205 is formed on the inner shell surface 4006 and is configured to electrically conduct current delivered thereto. Accordingly the TFTE actuators 100 can be disposed directly on the electrically conductive trace 205 such that the TFTE actuators 100 are connected in electrical series with one another.

Each of the TFTE actuators 100 are configured to generate one or both of a heating effect and a cooling effect in response to receiving an electrical current. According to a non-limiting embodiment, each of the TFTE actuators 100 includes a p-type controlled hierarchical engineered superlattice structure (CHESS), and an n-type CHESS. Each of the p-type CHESS and the n-type CHESS includes a thin-film thermoelectric material having a material thickness. Accordingly, the cooling speed of each of the TFTE actuators 100 is inversely proportional to the material thickness. For example, the cooling speed is defined as a squared value of the material thickness.

According to a non-limiting embodiment, the interactive reality device 4000 includes a controller 4012 and one or more sensors 4014. The controller 4012 is in signal communication with the electrical electrically conductive trace 205 to deliver the electrical current to the plurality of TFTE actuators 100. The sensor 4014 is configured to measure a temperature associated with one or both of the heating effect and the cooling effect generated by the plurality of TFTE actuators 100 and to output a feedback signal indicative of the measured temperature to the controller 4012.

According to one or more non-limiting embodiments, one or more of the TFTE actuators includes a pressure-inducing mechanical actuator configured to generate a tactile effect. The plurality of TFTE actuators 100 are configured to generate the tactile effect simultaneously with the heating effect or the cooling effect described herein. In this manner, the interactive reality device 4000 can increase modalities by a factor of 5 (e.g., only tactile, only cooling, cooling and tactile simultaneously, only heating, and heating and tactile simultaneously) compared to conventional interactive reality devices that provide only tactile feedback. Also, the capability of the interactive reality device 4000 to combining the range of tactile sensations (e.g., pressure) and range of temperatures substantially increases the possibilities for AR/VR modalities.

Thus, as shown and described herein, various non-limiting example embodiments provide a fast-rate thermoelectric device capable of quickly applying a rapid thermal response to a surface almost instantaneously. The thermoelectric device includes an array of individual fast-rate thermoelectric actuators, which are connected to one another. A voltage potential is applied across the array to induce an electrical flow through the individual fast-rate thermoelectric actuators. The current flow induces the rapid thermal response (e.g., a rapid heating effect and/or a rapid cooling effect) that is produced from the surface of the fast-rate thermoelectric device. The fast-rate thermoelectric device described herein can be placed directly against a surface including, but not limited to, human skin. In this manner, the fast-rate thermoelectric device can rapidly convey changes in thermal sensation to individuals through contact with the skin for many applications including, but not limited to, biomedical thermotactile applications.

In the present description, the terms "computer program medium," "computer usable medium," "computer program product," and "computer readable medium" are used to generally refer to media such as memory. Computer programs (also called computer control logic) are stored in memory. Such computer programs, when run, enable the computer system to perform the features of the example embodiments described herein. In particular, the computer programs, when run, enable the controller to perform the features and operations described herein. Accordingly, such computer programs can controllers of the computer system.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or "flash" memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, a process, a method, an article, or an apparatus that comprises a list of elements is not necessarily limited to only those elements but can include other elements not expressly listed or inherent to such composition, mixture, process, method, article, or apparatus.

The terminology used herein is for the purpose of describing particular embodiments only and is not intended to be limiting of the described example embodiments. As used herein, the singular forms "a", "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

Additionally, the term "example" or "exemplary" (and variations thereof) are used herein to mean "serving as an example, instance, or illustration." Any embodiment or design described herein as an "example" or "exemplary" is not necessarily to be construed as preferred or advantageous over other embodiments or designs. The terms "at least one," "one or more," and variations thereof, can include any integer number greater than or equal to one, e.g., one, two, three, four, etc. The terms "plurality" and variations thereof can include any integer number greater than or equal to two, e.g., two, three, four, five, etc. The term "connection" and variations thereof can include both an indirect "connection" and a direct "connection."

The terms "about," "substantially," "approximately," and variations thereof, are intended to include the degree of error associated with measurement of the particular quantity based upon the equipment available at the time of filing the application.

The phrases "in signal communication," "in communication with," "communicatively coupled to," and variations thereof can be used interchangeably herein and can refer to any coupling, connection, or interaction using electrical signals to exchange information or data, using any system, hardware, software, protocol, or format, regardless of whether the exchange occurs wirelessly or over a wired connection.

Example embodiments are described herein with reference to flowchart illustrations and/or block diagrams of methods, apparatus (systems), and computer program products according to example embodiments. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various example embodiments. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The corresponding structures, materials, acts, and equivalents of any means or step plus function elements in the claims below are intended to include any structure, material, or act for performing the function in combination with other claimed elements as specifically claimed. The description of the example embodiments has been presented for purposes of illustration and description, but is not intended to be exhaustive or limited to the present teachings in the form disclosed. Many modifications and variations will be apparent to those of ordinary skill in the art without departing from the scope and spirit of the present disclosure described and shown herein. The example embodiments were chosen and described in order to best explain the principles of the present disclosure and the practical application thereof, and to enable others of ordinary skill in the art to understand the present disclosure for various embodiments with various modifications as are suited to the particular use contemplated.

What is claimed is:

1. A thermotactile stimulation prosthesis comprising:
a prosthesis extremity having a prosthesis interface configured for attachment to a human limb; and
a thermoelectric actuator array coupled to the prosthesis interface and configured to establish a noninvasive thermoneural human-machine interface capable of providing sensations of temperature to the human limb,
wherein the thermoelectric actuator array comprises a plurality of thin-film thermoelectric (TFTE) actuators configured to generate one or both of a heating effect and a cooling effect in response to an electrical current,
wherein the plurality of TFTE actuators each include a p-type controlled hierarchical engineered superlattice structure (CHESS), and an n-type CHESS, and wherein each of the p-type CHESS and the n-type CHESS comprises a thin-film thermoelectric material having a material thickness, and
wherein the p-type CHESS and the n-type CHESS each include superlattice periods of varying thickness and associated layers of varying thickness to scatter a range of phonons.

2. The thermotactile stimulation prosthesis of claim 1, further comprising:
at least one sensor configured to measure a temperature associated with one or both of the heating effect and the cooling effect and to output a feedback signal indicative of the measured temperature; and
a controller in signal communication with the thermoelectric actuator array and the at least one sensor, the controller configured to control one or more of the TFTE actuators of the plurality of TFTE actuators based on the measured temperature indicated by the feedback signal.

3. The thermotactile stimulation prosthesis of claim 2, wherein the controller is configured to control the electrical current based at least in part on the feedback signal to control the one or both of a heating effect and a cooling effect.

4. The thermotactile stimulation prosthesis of claim 3, further comprising:
a hollow shell extending from a distal end supporting the prosthesis extremity to a proximate end, the hollow shell including an outer shell surface and an inner shell surface, the inner shell surface opposing the outer shell surface, surrounding an inner void; and
a socket disposed in the inner void, the socket extending from a distal end to a proximate end that defines an opening configured to receive a residual limb, the socket having a socket outer surface and a socket inner surface, the socket inner surface opposing the socket outer surface, to establish contact with the residual limb,
wherein the thermoelectric actuator array is disposed on the socket inner surface and is configured to establish the noninvasive thermoneural human-machine interface capable of providing sensations of temperature to the residual limb.

5. The thermotactile stimulation prosthesis of claim 3, wherein a cooling speed of each of the TFTE actuators is inversely proportional to the material thickness.

6. The thermotactile stimulation prosthesis of claim 5, wherein the cooling speed is defined as a squared value of the material thickness.

7. The thermotactile stimulation prosthesis of claim 3, wherein the controller is configured to control one or more of the TFTE actuators to apply one or both of heat pulses and cold pulses to perform one or a combination of regenerate nerve damages, check human responses, and nerve damage identification.

8. An interactive reality device comprising:
a hollow shell configured to fit with a human appendage, the hollow shell including an outer shell surface and an inner shell surface, the inner shell surface opposing the outer shell surface, surrounding an inner void configured to receive the human appendage; and
a plurality of a plurality of thin-film thermoelectric (TFTE) actuators disposed on the inner shell surface, the plurality of TFTE actuators configured to establish a noninvasive thermoneural human-machine interface capable of providing sensations of temperature to the human appendage,
wherein the TFTE actuators of the plurality of TFTE actuators each include a p-type controlled hierarchical engineered superlattice structure (CHESS), and an n-type CHESS,
wherein each of the p-type CHESS and the n-type CHESS comprises a thin-film thermoelectric material having a material thickness, and
wherein the p-type CHESS and the n-type CHESS each include superlattice periods of varying thickness and associated layers of varying thickness to scatter a range of phonons.

9. The interactive reality device of claim 8, further comprising an electrically conductive trace formed on the inner shell surface, wherein the plurality of TFTE actuators are disposed directly on the electrically conductive trace such that the TFTE actuators are connected in electrical series with one another.

10. The interactive reality device of claim 9, wherein the TFTE actuators are configured to generate one or both of a heating effect and a cooling effect in response to receiving an electrical current.

11. The interactive reality device of claim 10, wherein a cooling speed of each of the TFTE actuators is inversely proportional to the material thickness.

12. The interactive reality device of claim 11, wherein the cooling speed is defined as a squared value of the material thickness.

13. The interactive reality device of claim 10, further comprising a controller in signal communication with the electrically conductive trace to deliver the electrical current to the plurality of TFTE actuators.

14. The interactive reality device of claim 13, further comprising at least one sensor configured to measure a temperature associated with one or both of the heating effect and the cooling effect generated by the plurality of TFTE actuators and to output a feedback signal indicative of the measured temperature to the controller.

15. The interactive reality device of claim 8, wherein the plurality of TFTE actuators include a pressure-inducing mechanical actuator configured to generate a tactile effect.

16. The interactive reality device of claim 10, wherein the plurality of TFTE actuators include a pressure-inducing mechanical actuator configured to generate a tactile effect and are configured to generate the tactile effect simultaneously with the heating effect or the cooling effect.

* * * * *